(12) United States Patent
Kim et al.

(10) Patent No.: US 8,513,409 B2
(45) Date of Patent: Aug. 20, 2013

(54) INTROVERTED CB[N] COMPOUNDS

(75) Inventors: Kimoon Kim, Pohang (KR); Sang-Kyu Park, Seoul (KR); Young Ho Ko, Pohang (KR); Hyunuk Kim, Pohang (KR); Youngkook Kim, Pohang (KR); Narayanan Selvapalam, Pohang (KR); Lyle David Isaacs, Bethesda, MD (US); Simin Liu, Metairie, LA (US)

(73) Assignees: University of Maryland, College Park, MD (US); Pohang University of Science and Technology, Gyungbuk (KR)

( * ) Notice: Subject to any disclaimer, the term of this patent is extended or adjusted under 35 U.S.C. 154(b) by 997 days.

(21) Appl. No.: 11/989,200

(22) PCT Filed: Jul. 24, 2006

(86) PCT No.: PCT/US2006/028841
§ 371 (c)(1),
(2), (4) Date: Sep. 21, 2009

(87) PCT Pub. No.: WO2007/014214
PCT Pub. Date: Feb. 1, 2007

(65) Prior Publication Data
US 2010/0010215 A1  Jan. 14, 2010

Related U.S. Application Data

(60) Provisional application No. 60/701,732, filed on Jul. 22, 2005, provisional application No. 60/736,991, filed on Nov. 15, 2005.

(51) Int. Cl.
*C07D 257/10* (2006.01)

(52) U.S. Cl.
USPC .......................................................... 540/472

(58) Field of Classification Search
USPC .............................................. 540/472
See application file for complete search history.

(56) References Cited

PUBLICATIONS

Day et al. "Controlling Factors in the Synthesis of Cucurbituril and Its Homologues" Journal of Organic Chemistry, 2001, vol. 66, pp. 8904-8100.*

Lee et al. "Cucurbituril Homologues and Derivatives: New Opportunities in Supramolecular Chemistry" Acc. Chem. Res. 2003, 621-630.*

Day et al., "Controlling Factors in the Synthesis of Cucurbituril and Its Homologues", Journal of Organic Chemistry, 2001, vol. 66, pp. 8904-8100.

* cited by examiner

*Primary Examiner* — Joseph Kosack
(74) *Attorney, Agent, or Firm* — William E. Beaumont

(57) ABSTRACT

Inverted cucurbituril compounds having at least one pair of hydrogen atoms protruding into an internal molecular cavity thereof.

13 Claims, 15 Drawing Sheets

INTROVERTED CB[N] COMPOUNDS

CROSS REFERENCE TO RELATED CASES

This application claims the benefit of U.S. Provisional Application Ser. Nos. 60/701,732, filed Jul. 22, 2005, and 60/736,991, filed Nov. 15, 2005, which are both incorporated by reference herein in their entirety. This application also incorporates pending U.S. application Ser. No. 10/933,538, herein in the entirety.

STATEMENT REGARDING FEDERALLY SPONSORED RESEARCH

This invention was made with government support under R01GM61854 awarded by the National Institutes of Health (NIH). The government has certain rights in the invention.

BACKGROUND OF THE INVENTION

1. Field of the Invention

The present invention relates to introverted cucurbituril CB[n] compounds and/or derivatives, and methods of making and using the same as well as to an improved synthesis of higher cucurbituril compounds.

2. Description of the Background

Cucurbituril (CB[n]) compounds are macrocyclic compounds containing glycouril repeat units, and afford an advantageous alternative to cyclodextrins in creating supramolecular constructs. Cucurbiturils were first synthesized in 1905 by Behrend, although the molecular structure thereof was not elucidated until 1981. Later synthetic efforts to prepare CB[n] compounds demonstrated the complexity and unreliability of conventional preparatory methods. See Day et al. J., Org. Chem. 2001, 8094-8100, and Lee et al., Acc. Chem. Res. 2003, 621-630. Kim et al. J.A.C.S. 2000, 122, 540-541. More recently, reliance on a methylene-bridged glycouril dimer substructure as the fundamental building block of CB[n] compounds has led to an unprecedented level of control in the synthesis of CB[n] compounds and their internal cavity volumes. See U.S. application Ser. No. 10,933, 538, incorporated herein in the entirety.

Generally, CB[n] compounds have the formula shown in FIG. 1(a): wherein in the CB[n] formula, corresponding n values are shown for exemplary CB[n] compounds CB[5]-CB[8].

Also known are certain CB[n] derivatives shown in FIG. 1(b), wherein in the CB[n] formula, corresponding n values are shown for exemplary derivatives CB[5] and CB[6].

Importantly, in all of the known CB[n] compounds or CB[n] derivatives, all functional groups point outward from the CB[n] molecule as shown in FIGS. 1(a) and 1(b). That is, the functional groups protrude from the external surface of the molecule into exo-molecular space. However, it would be advantageous to be able to prepare CB[n] compounds or CB[n] derivatives having functional groups that point into the molecular cavity, i.e., inverted CB[n] compounds or CB[n] derivatives.

Inverted CB[n] compounds or CB[n] derivatives would, in fact, provide numerous advantages, such as:

1) Functional groups which point into the cavity of a cucurbituril compound which would enable:
   a) monitoring of complexation by $1_H$ NMR spectroscopy of H-atoms, for example, pointing into the CB[n] internal cavity, and
   b) use of introverted functional groups to enhance binding and/or catalytic processes in a manner similar to enzymes.
2) Fine tuning (on the angstrom length scale) of the size of the cavity of the cucurbituril, which is not possible with the known "extroverted" cucurbiturils having functional groups on the external molecular surface.
3) Two ureidyl carbonyl functional groups of monointroverted CB[6], for example, which are exposed to solvent which indicates that they may undergo selective functionalization reactions which would enable:
   a) their selective derivatization to thiourea, guanidinium, and other functional groups, and
   b) their attachment to suitable solid phases e.g. resin beads, silica gels, and surfaces.
4) Monointroverted CB[6] is thermodynamically less stable that CB(6) itself, for example, which enables the investigation of its chemistry with potential application in the following areas:
   a) the mechanism of CB[n] formulation,
   b) the selective production of mono- and multiply functionalized CB[n], and of bis, tris, and multiply covalently connected CB[n], by tailor-made synthetic approaches, and
   c) the production of fragments of the cucurbit[n]uril skeleton which may have binding properties as unusual as the CB[n] family themselves.

However, to date such introverted CB[n] compounds and derivatives have been unknown.

Thus, a need exists for inverted CB[n] compounds and/or CB[n] derivatives which would have the structural and reactive characteristics noted above, and which could be prepared in a reliable manner.

SUMMARY OF THE INVENTION

Accordingly, it is an object of the present invention to provide inverted (also herein called "introverted") or i-CB[n] compounds and/or i-CB[n] derivatives.

It is also an object of the present invention to provide various methods for preparing the inverted CB[n] compounds and/or CB[n] derivatives.

It is, moreover, an object of the present invention to provide various methods of using the inverted CB[n] compounds and/or CB[n] derivatives.

The above objects and other described hereinbelow are provided, in part, by inverted CB[n] compounds and/or inverted CB[n] derivatives thereof having one or more hydrogen atoms or functional groups protruding into the internal CB[n] cavity.

DETAILED DESCRIPTION

The present invention provides, in part, an improved synthetic procedure for preparing higher cucurbituril (CB[n]) compounds, and, notably, inverted CB[n] compounds. As used herein, the term "higher" CB[n] compound and/or derivative means compounds and/or derivatives where n has an integral value of from 8 to 25, preferably from 8 to 20, most preferably from 8 to 16. However, all integral n values of 5, 6, 7, 8, 9, 10, 11, 12, 13, 14, 15, 16, 17, 18, 19, 20, 21, 22, 23, 24 and 25 are explicitly contemplated.

Figure 1B:
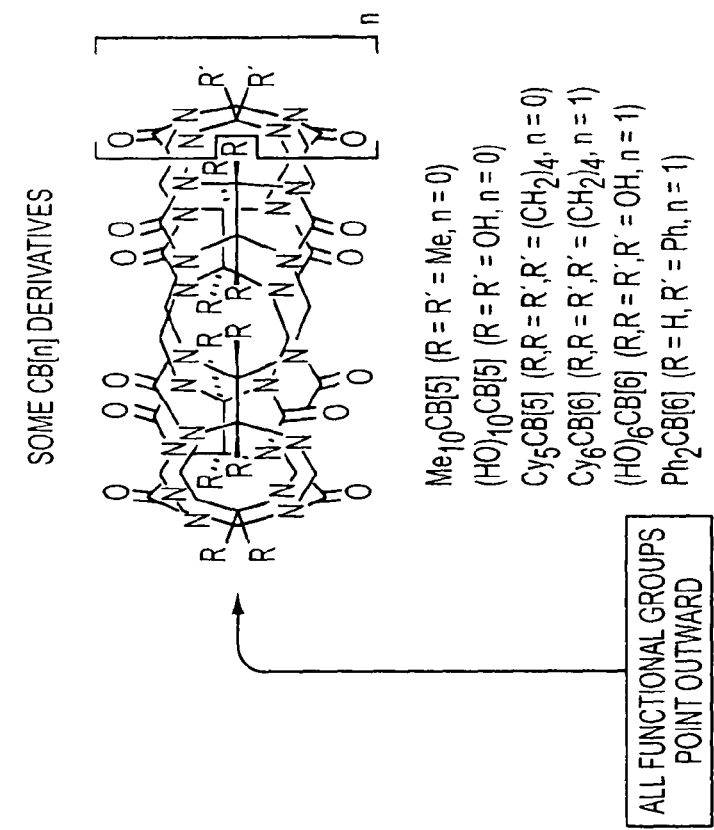
FIG. 1(b) shows the same for some known CB[n] derivatives.
Figure 1A:
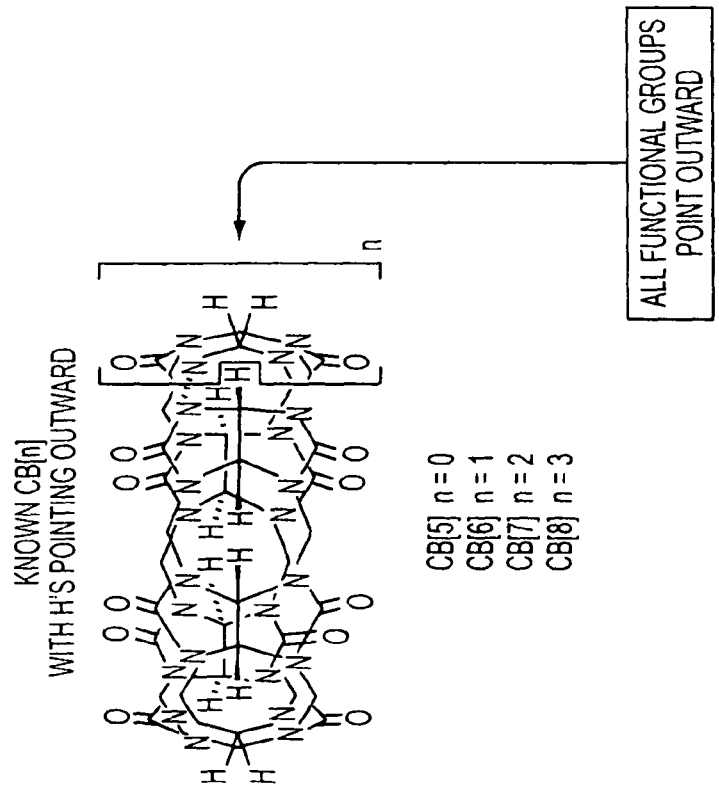
FIG. 1(a) shows the structural formulae of known CB[n] compounds.

From FIG. 1(a), it may be readily appreciated that in the cucurbituril ring system as depicted, CB[5] corresponds to an n value of 0, CB[6] to where n is 1, CB[7] to where n is 2, and CB[8] to where n is 3. Hence, the compound CB[12] corresponds to a n value of 7, for example.

As used herein, the designation "CB[n]" refers to cucurbituril compounds of the formulae depicted in FIG. 1(a) for any given n value. The designation "CB[n]" may also refer to cucurbituril derivatives for any given n value. In such cases, the derivative is specified as having a particular and defined functionality.

In the following description, regular or "extroverted" CB[n] compounds and/or derivatives means that all —H atoms and/or functional groups replacing —H atoms protrude or point out from the cucurbituril molecule. These compounds or derivatives are indicated as "CB[n]."

The present invention also provides inverted or introverted CB[n] compounds and CB[n] derivatives. As used herein, the terms "inverted" and "introverted" are used interchangeably to refer to cucurbituril compounds or derivatives thereof having at least one hydrogen atom or functional group, respectively, which protrudes or points into the internal volume cavity of the cucurbituril molecule. Preferably, at least two inverted hydrogen atoms of functional groups protrude into the internal volume cavity of the cucurbituril molecule. For convenience, all of the inverted cucurbituril compounds and derivatives described hereinbelow may also be conveniently labeled with the prefix "i," i.e., i-CB[6] or i-CB[12], for example. In each case, the prefix "i" refers to the fact that the CB[n] compound has at least one —H atom protruding or pointing into the internal volume cavity of the CB[n] molecule. Preferably, the i-CB[n] compound will have more than one —H atom protruding or pointing into the internal volume cavity of the CB[n] molecule.

As noted above, the prefix "i," as used herein, may also refer to the fact that a CB[n] derivative has at least one functional group replacing an —H atom, which group protrudes or points into the internal volume cavity of the CB[n] molecule.

Additionally, as used herein, the term "derivative" refers to a CB[n] compound or i-CB[n] compound where at least one —H atom, which protrudes or points into the internal cavity volume of the molecule, is replaced with a functional group. In the CB[n] and i-CB[n] derivatives of the present invention, it is preferred that more than one —H atom, protruding or pointing into the internal cavity volume of the molecule, is replaced with a functional group.

Any functional group or groups may be used as a replacement for the one or more —H atoms which protrude into the internal cavity volume.

For the sake of brevity, as used herein the term "internal" hydrogen(s) or "internal" functional group(s) is used to mean such —H atoms(s) or functional group(s) which protrude or point into the cucurbituril molecular cavity.

For example, the one or more internal functional groups may be lower alkyl, $C_6$-$C_{14}$ aryl and/or arylalkyl, hydroxy, amino, halo, or nitro.

Examples of lower alkyl are methyl, ethyl, n-propyl, isopropyl or n-butyl.

Examples $C_6$-$C_{14}$ aryl include phenyl or naphthyl, while examples of $C_6$-$C_{14}$ arylalkyl include lower alkyl phenyl, such as methylphenyl (toluoyl) or ethylphenyl, for example.

Figure 2:
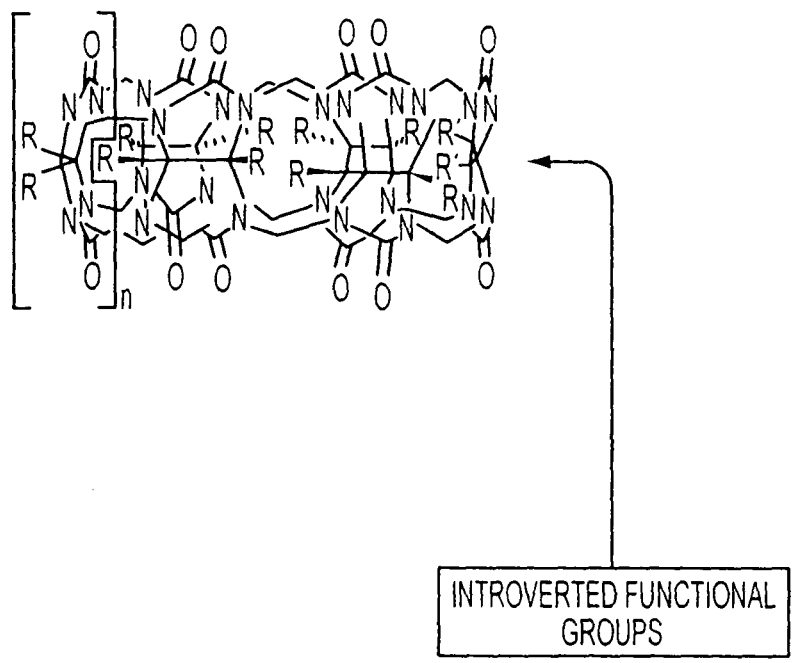
FIG. 2 illustrates the general formula for introverted CB[n] compounds and/or derivatives, which the functional groups R have replaced —H atoms.

Generally, the i-CB[n] compounds of the present invention have the formula shown in FIG. 2 where n may be an integer of from 0 to up to at least 25. However, n is preferably an integer of from 6 to 20, most preferably from 8 to 16.

Additionally, it is explicitly disclosed herein that the inverted or introverted or i-CB[n] compounds and/or derivatives of the present invention may be either mono-introverted or multiply-introverted. As used herein, the term "mono-introverted" means that the —H atoms for an i-CB[n] compound or the functional groups of a single glycouril ring framework are pointed inward into the internal volume cavity of the molecule.

As used herein, the term "multiply-introverted" means that the —H atoms for an i-CB[n] compound or the functional groups of multiple, i.e., more than one, glycouril ring framework are pointed inward into the internal volume cavity of the molecule.

Notably, as shown in the above i-CB-[n] formula, either or R or $R^1$ or both may be functional groups as defined above which replace —H atoms.

In FIG. 2 for the i-CB[n] compounds and/or derivatives of the present invention, as noted n may be an integer of from 5 to at least 25, and preferably from 6 to 20, and most preferably from 8 to 16. However, i-CB[n] compounds and derivatives of all functional groups as defined above are explicitly contemplated for n values of 5, 6, 7, 8, 9, 10, 11, 12, 13, 14, 15, 16, 17, 18, 19 20, 21, 22, 23, 24, and 25.

Preparation of Inverted Cucurbituril Compounds and Derivatives Thereof

The present invention achieves a number of important objectives.

First, the present invention affords an improved synthesis for higher CB[n] compounds and/or derivatives generally.

Second, the present invention affords a synthesis of large inverted cucurbituril compounds and derivatives thereof under anhydrous conditions.

In studies conducted under anhydrous acidic conditions we have elucidated two key steps in the mechanism of CB[n] formation. We have determined that the larger cucurbitural homologs (CB[n] n>8), including inverted CB[n] compounds, are most efficiently prepared under anhydrous acidic conditions, and that inverted or introverted, i.e., i-CB[n] compounds, can also thereby be prepared. Thus, the present invention explicitly contemplates the selective preparation of the larger CB[n] (n=8, 9, 10, 11, etc.) compounds, including inverted CB[n] compounds and/or derivatives, under anhydrous acidic conditions.

Third, the present invention affords a synthesis for persubstituted inverted cucurbiturils using glycouril monomers.

To date, a limited number of CB[n] derivatives have been prepared from functionalized glycoluril derivatives (R=Me and —$(CH_2)_4$—). We have determined that R groups that destabilize adjacent carbocations (e.g. R=$CO_2Et$) are more efficient substrates for the formation of the key methylene bridge glycoluril substructure than are glycoluril derivatives bearing electron donating Ph or alkyl groups. We also describe herein novel glycoluril monomers (imides, diamides, and acids) and use them to prepare new persubstituted CB[n] derivatives.

Fourth, the present invention provides a synthetic scheme that provides for control over size, and both degree of and pattern of substitution CB[n] compounds, including [n] i-CB compounds.

Our results indicate that under both aqueous and anhydrous acidic conditions, the size, number, and pattern of substituents on CB[n] derivatives is controllable by the judicious choice of reactants and reaction conditions. We describe a building block approach for the tailor-made synthesis of CB[n] derivatives including those with internally directed functional groups. As mentioned above, anhydrous acidic conditions are advantageously used to avoid degradation of any water-sensitive functional groups present such as ester groups.

Fifth, the present invention provides hydrazides as glycouril surrogates in inverted cucurbituril syntheses.

We disclose herein that arylhydrazides function as glycoluril substitutes in typical methylene bridge forming reactions. We have extended this work to the preparation of CB[n] derivatives incorporating one or more aromatic rings into their macrocyclic structure. These CB[n] derivatives greatly expand the range of applications of CB[n] by providing functionalization sites along their rims which complement those that already exist around the equatorial or mid-section of the CB[n] molecule.

Figure 3A:
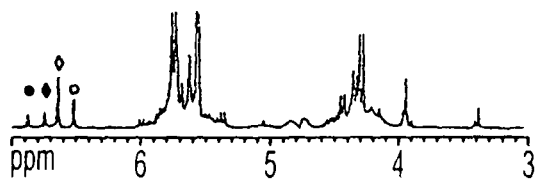
FIG. 3 illustrates same advantageous features of i-CB[n] compounds and derivatives.
Figure 3B:
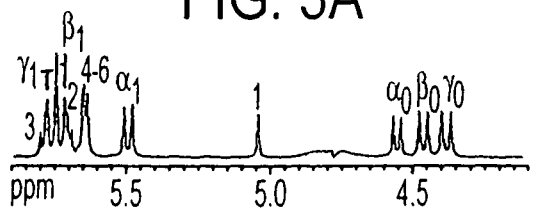
Figure 3C:
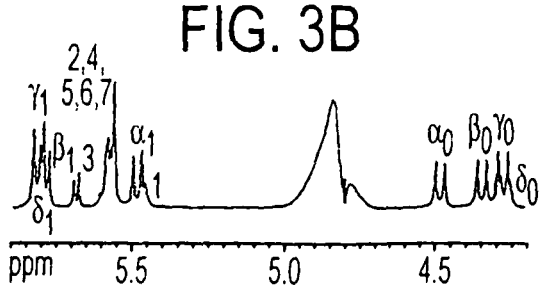

FIG. 3 illustrates the advantageous features of the i-CB[n] compounds and derivatives of the present invention.

Additionally, the present invention also provides various advantageous chemical transformations using the inverted CB[n] compounds and/or derivatives described herein. FIG. 3 illustrates some of the useful transformations afforded with the inverted CB[n] compounds and/or derivatives.

Each of the above aspects of the present invention will now be discussed in detail.

A. Synthesis Under Anhydrous Conditions

The complexity associated with CB[n] synthesis—formation of n 8-membered rings and 2n methylene bridges with control over the relative stereochemistry of n glycoluril rings—has rendered experimental attempts to elucidate the mechanism of CB[n] formation difficult. Our approach to the synthesis of CB[n] compounds and other glycoluril derivatives with interesting molecular recognition properties relies on the identification of a methylene bridged glycoluril dimer substructure as the fundamental building block of CB[n]. As a result of this synthetic simplification, the complexity of the reaction—the formation of one ring, two methylene bridges, and control and over the relative stereochemistry of two glycoluril rings—was substantially reduced relative to the synthesis of CB[n]. See U.S. application Ser. No. 10/933,538. As a result, we have been able to address three key mechanistic questions that have been elusive in the chemistry of CB[n] itself. First, both S-shaped and C-shaped methylene bridged glycoluril oligomers form as kinetic products during CB[n] synthesis in approximately a 1:1 ratio. Second, the S-shaped and C-shaped diastereomers are in equilibrium with one another, and the equilibrium favors the C-shaped diastereomers—the thermodynamic product—in a 95:5 ratio. Third, the mechanism for the interconversion of the S-shaped and C-shaped diastereomers under anhydrous acidic conditions in a diastereoselective, intramolecular reaction.

Scheme 1. Diastereoselective, intramolecular S- to C- shaped isomerization reaction (±)-11.

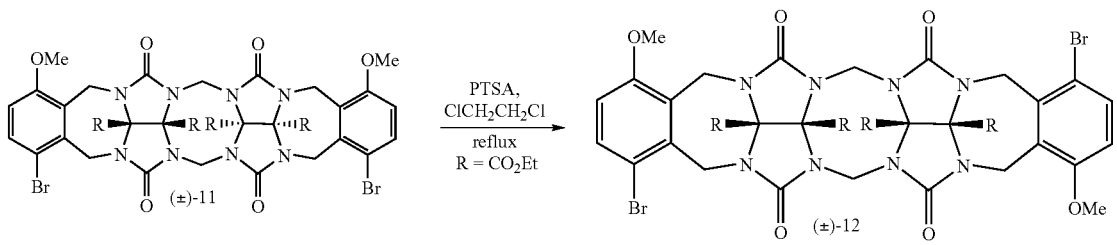

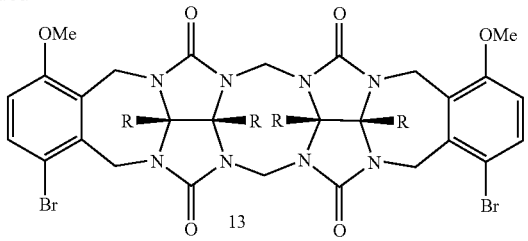

(not formed)

Scheme 1 shows one of several S- to C-shaped isomerization reactions. As can be readily seen during the S- to C-shaped isomerization, the "methoxy labels" of (±)-11 undergo clean transposition to the opposite side of the molecule in (±)-12 when the reaction is conducted under anhydrous conditions. Scheme 2 summarizes the stereochemical outcome of three potentially viable mechanisms: mechanism 1, mechanism 2, mechanism 3. The stereochemical outcome indicates that mechanism 3 is dominant under our standard isomerization conditions (ClH$_2$CH$_2$Cl, anh. PTSA, reflux). When the isomerization of (±)-11 is conducted with added H$_2$0, we observed the formation of both (−±)12 and 13 indicating that mechanism 1 is also operative.

The fact that the isomerization of methylene bridged glycoluril dimmers follows mechanism 3 is not only useful in the synthesis of our compounds, but is important for the tailored synthesis of CB[n] and its derivatives. For example, Day and co-workers have recently shown that heating purified CB[8] in conc. HCl 100° C. results in the formation of CB[5], CB[6], and CB[7] (Scheme 3). In contrast, pure CB[5], CB[6], and CB[7] are stable under these conditions. These results require that two adjacent methylene bridges are broken and that one or more glycoluril rings are extruded. This type of reaction would likely follow a pathway related to mechanism 1. We have demonstrated that mechanism 1 is not operative in our system when we work under anhydrous acidic conditions. In aqueous acid, it is likely that H$_2$O can compete with the internal N and O nucleophiles of mechanism 3 for the capture of 19 (Scheme 2), effectively forcing fragmentation of the methylene bridges by a variation of mechanism 1. In the absence of competing nucleophiles, under anhydrous acidic conditions, CB[n] (n>8) and derivatives display enhanced stability. This facilitates the preparation of higher CB[n] compounds in a controllable manner when using anhydrous acidic conditions where water-sensitive functional groups are present. If such groups are not present acidic aqueous conditions may be used.

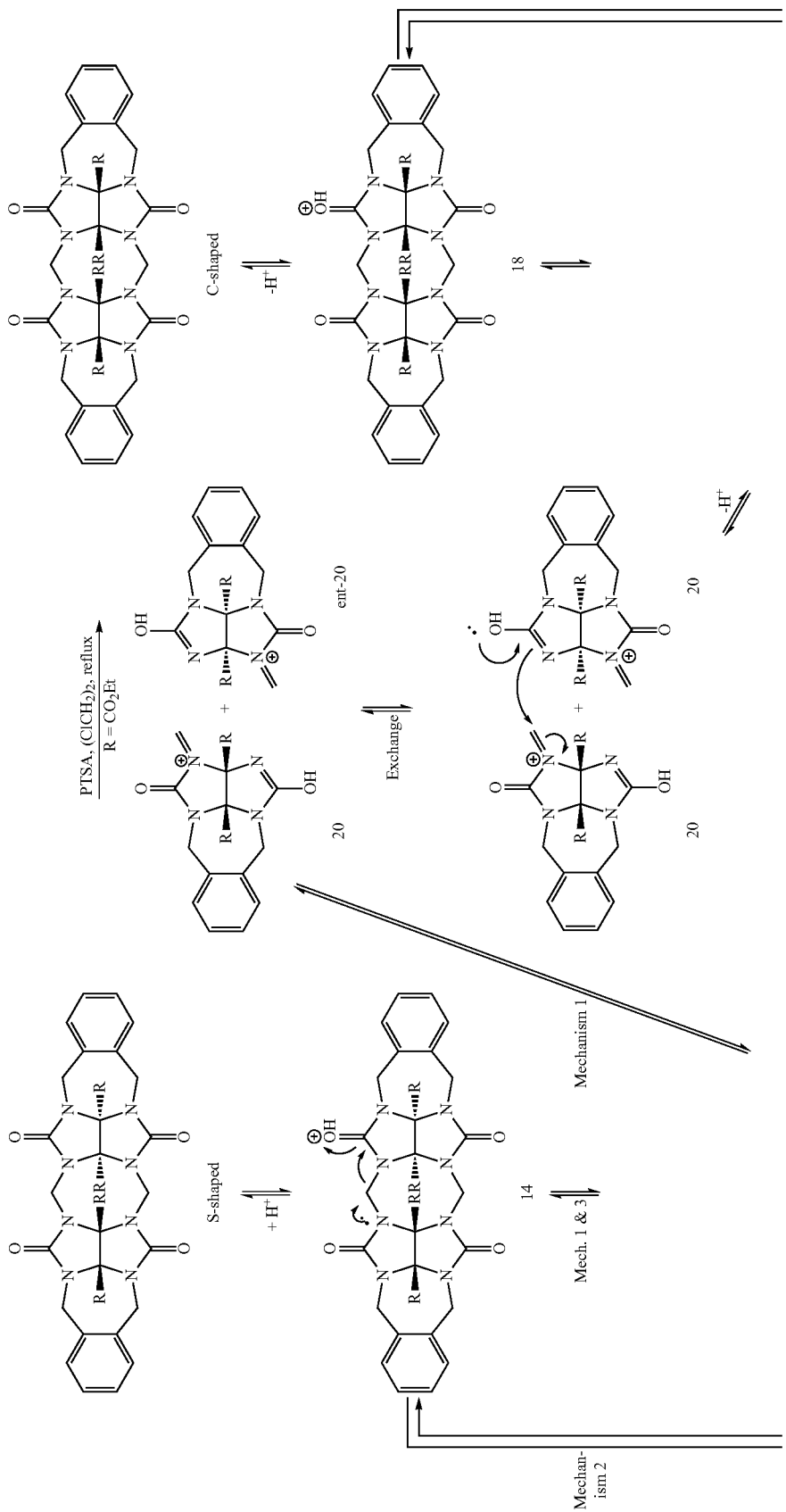
Scheme 2. Three different mechanistic proposals for the S- to C- isomerization that are distinguishable based on the isomerization reaction presented in Scheme 4. Under anhydrous acidic conditions mechanism 3 is dominant.

-continued
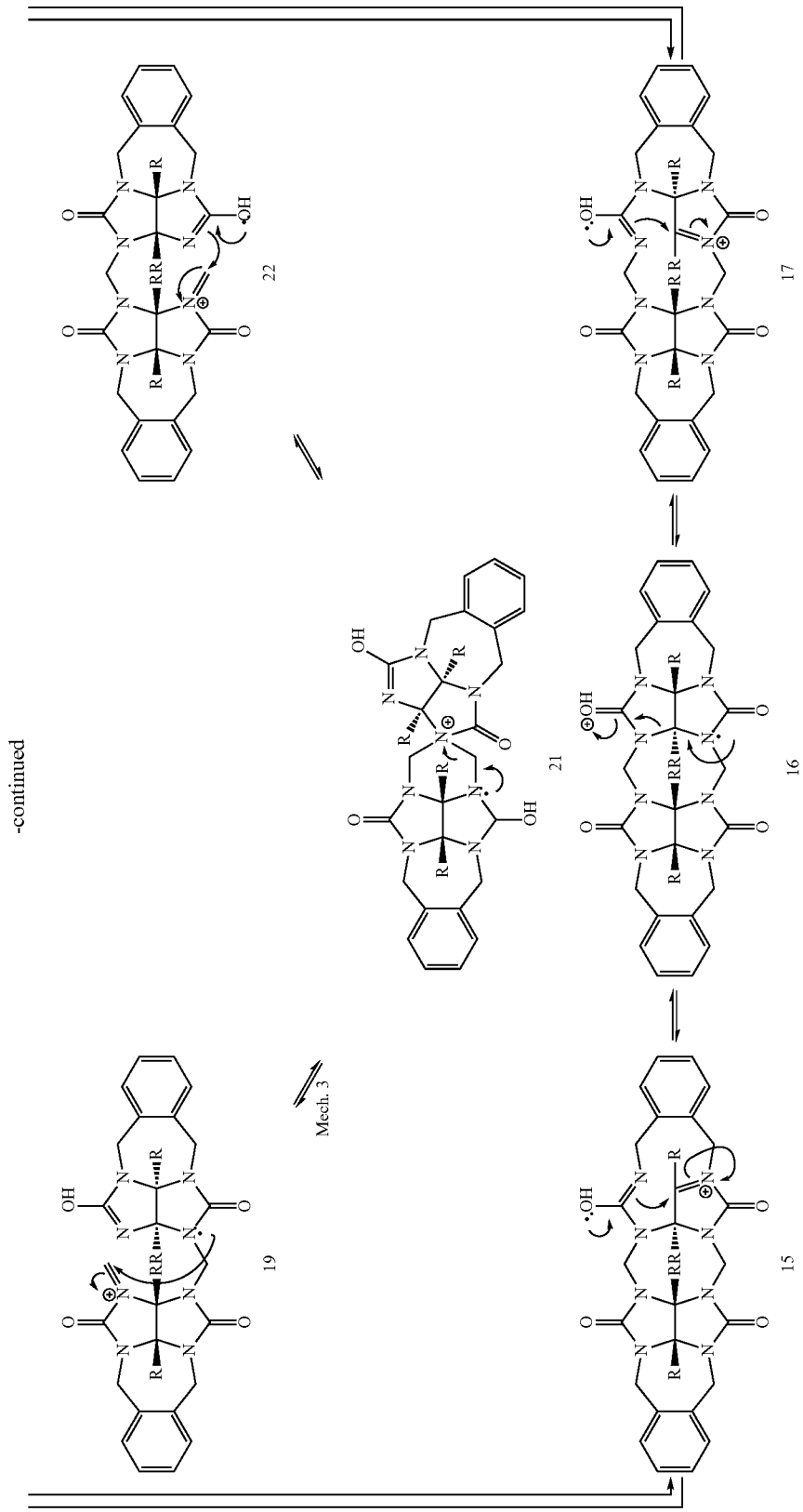

Scheme 3 shows the conversion of CB[8] into CB[5], CB[6], and CB[7] under aqueous acidic conditions reported by Day. As an initial demonstration that the higher CB[n] displays enhanced stability under conditions where mechanism 3 (Scheme 2) dominates, we heated purified CB[8] under anhydrous acidic conditions. By "anhydrous acidic conditions," we mean that in initial attempts "standard conditions" (ClCH$_2$CH$_2$Cl, anh. PTSA, reflux) are used, and if solubility problems occur then neat anhydrous PTSA (m.p. 38° C.) and/or CH$_3$SO$_3$H may be used. Based on results, CB[8] is stable to these conditions as depicted in Scheme 3.

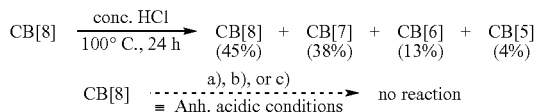

Conditions: a) ClCH$_2$CH$_2$Cl, anh. PTSA, reflux, b) anh. PTSA, heat c) anh. CH$_3$SO$_3$H, heat.

B. Synthesis of Higher CB[n] Compounds and Derivatives Thereof

Even though the original CB[6] synthesis reported by Behrend proceeds in two steps, all subsequent procedures occur in a single step under strongly acidic aqueous conditions. Based on our results, we can suppress fragmentation reactions of methylene bridged glycoluril oligomers and effectively force the S- to C-isomerization reaction to proceed intramolecularly. As methylene bridged glycoluril oligomers cyclize by end-end coupling, the length of the oligomer controls the size of the formed CB[n]. Scheme 4, depicts the oligomerization of glycoluril $^3$H using the conditions described by Behrend to obtain 8n. Then, 8, is cyclized to yield CB[n] either alone, or under heterodimerization conditions in the presence of added $^3$H. The success of this route appears sensitive to the relative kinetics of S- to C-isomerization and cyclization versus further oligomerization. It is feasible to isomerize $23_n$ to the all C-shaped $23C_n$ under anhydrous acidic conditions. Compound $23C_n$ is preorganized for cyclization to CB[n], which could occur either by reaction with $(CH2))_n$ or with $24_H$ under anhydrous acidic conditions. We are thereby able to selectively obtain larger CB[n] compounds in this manner.

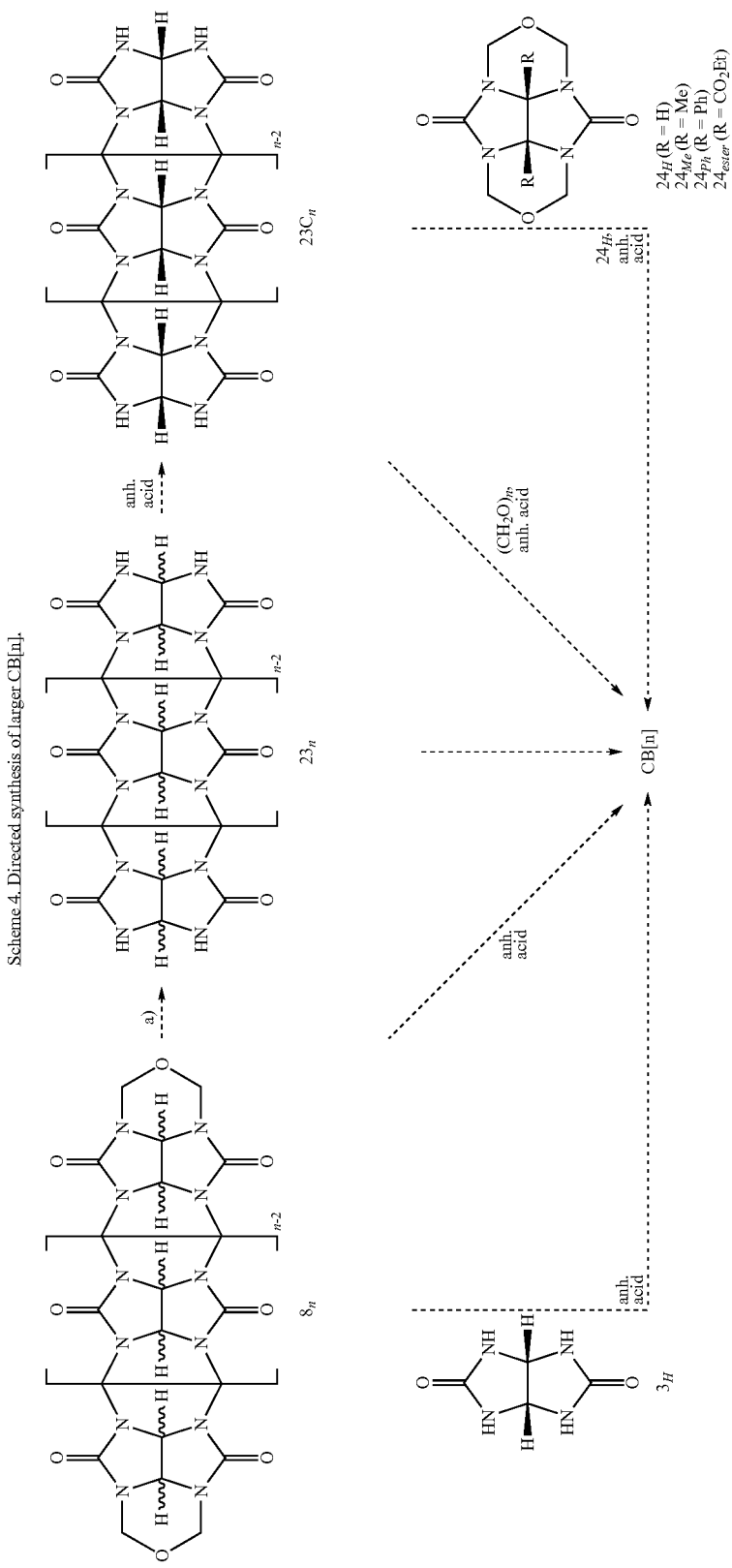

The identification of the different sized CB[n] is straightforward even in a crude reaction mixture because of a correlation between ring size (n) and $^{13}C$ chemical shift of the bridging chemical shift of the bridging methylene and glycoluril methane C-atoms. There are no significant problems with the spectroscopic analysis of these crude reaction mixtures, but, if necessary $^{13}C$, $^{2}H$, or $^{15}N$ labeled compounds may be selectively used by using commercially available ($^{13}CH_2O)_n$, $CD_2O)_n$, $H_2N^{13}CONH_2$, and $H_2\ ^{15}NCO^{15}NH_2$. The purification of known CB[n] compounds has been achieved in a variety of different ways, but the most reliable are recrystallization from hot aqueous acidic solutions, by chromatographic separation (using $H_2O/CH_3CN/HCO_2H$), by GPC (sephedex), and by ion-exchange chromatograpy (Dowex 50). The separation of reaction mixtures is feasible using one or more of these techniques.

C. Preparation of Glycoluril Monomer for the Synthesis of Persubstituted i-CB[n] Compounds and Derivatives Thereof There are, for example, three complementary synthetic routes for the preparation of methylene bridged glycoluril dimers (ex: 25S, 25C, and (±)-29C, Scheme 5). They are: 1) the homodimerization of compounds with free ureidyl NH groups (ex. 26 with paraformaldehyde, 2) the homodimerization of cyclic ethers (ex. 27) with the formal extrusion of 2 eq. of formaldehyde, and 3) the condensation reactions of 1 eq. of 27 with 1 eq. (±)-28. Method 3 is highly selective and yields the heterodimeric product (±)-29C preferentially.

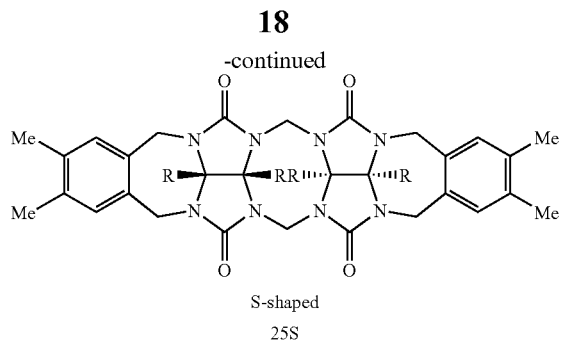

We have found that glycoluril derivatives bearing electron withdrawing carboxylic acid derivatives, such as —$CO_2Et$, on their convex face undergo clean dimerization reactions (Scheme 5) whereas glycoluril derivatives bearing substituents that stabilize adjacent positive charge (phenyl and cycloalkyl) dimerize poorly and with formation of aldehydic side products (±)-30. A mechanistic rationale for this observation is presented in Scheme 6. Imminiium ion (±)-31, obtained by protonation and ring opening of 32 could, conceivably, be transformed directly into (±)-30 by a hydride shift reaction. This explanation seems unlikely, however, because the R groups play no role, and we would also expect to observe aldehydic side products when R=$CO_2Et$. Alternatively, we postulate the formation of intermediate (±)-33. transformation of (±)-33 into (±)-30 can then occur by a cationic imino ene reaction. One would expect the carbocationic intermediate (±)-33 to be stabilized by phenyl or alkyl substituents and destabilized by electron withdrawing groups (R=CO$_2$Et). The relatively high energy of (±)-33$_{ester}$ precludes its formation and results inefficient dimerization reactions. This chemical rationale explains two disparate observations in CB[n] chemistry: 1) the relatively low yield obtained in the preparation of Cy$_6$CB[6] (16%) and Cy$_5$CB[5] (2%), and 2) the inability to prepare Ph$_{12}$CB[6]. This chemical rationale indicates that CB[n] formation is most successful for glycoluril derivatives bearing electron withdrawing groups on their convex face and least successful for those bearing substituents that stabilize adjacent positive charge.

groups on their convex face provide the most successful syntheses of CB[n] derivatives. The lower alkyl ester groups, such as ethyl ester groups of 3$_{ester}$ are ideally suited for this purpose: 1) they are electron withdrawing groups, 2) they provide good solubility in organic solvents, and 3) they are readily transformed into a variety of functional groups that would be useful for CB[n] synthesis. For example, 3$_{ester}$ easily transformed into the corresponding bis(cyclic ether) 24$_{ester}$ by treatment with paraformaldehyde in refluxing TFA (Scheme 7). Compound 24$_{ester}$ also undergoes deprotection to 24$_{CO2Li}$ and smooth conversion to diamides 24$_{Bu}$ and 24$_{amine}$ by heating in solutions of the neat amines. Alterna- Scheme 6. Proposed mechanism for the formation of aldehydic side product (±)-30.

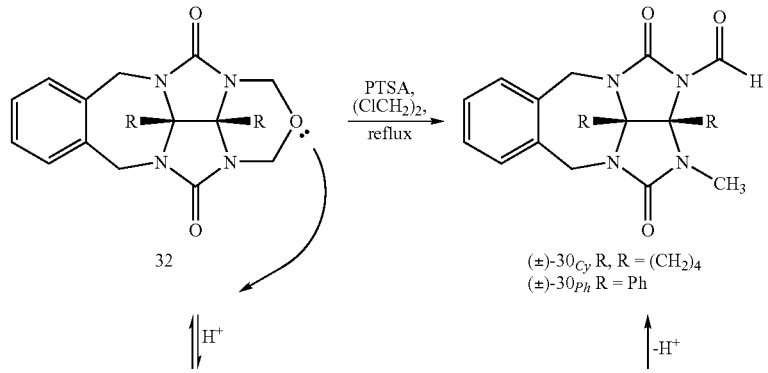

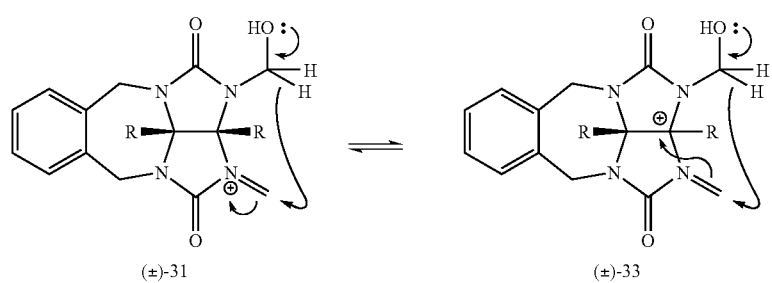

The mechanistic studies described above indicate that glycoluril derivatives bearing electron withdrawing functional tively, 3$_{ester}$ can be directed converted into diamides 3$_{Bu}$ and 3$_{amine}$ which bear potentially nucleophilic ureidyl NH groups. Diamides $3_{Bu}$ and $24_{amine}$ in good yield. These compounds—esters, acid, amides, and imides—all display enhanced solubility characteristics. In particular, we have found that $24_{ester}$ undergoes partial hydrolysis under strongly acidic aqueous conditions commonly used for CB[n] synthesis. Amides $24_{Bu}$ and $24_{amine}$ in contrast, do not undergo hydrolysis reactions, but undergo closure to the imides under strongly acidic conditions. Thus, imides $34_{Bu}$, $34_{amine}$, $35_{Bu}$, and $35_{amine}$, for example, are broadly compatible with both aqueous and anhydrous acidic CB[n] forming reactions.

and $35_{amine}$ are more resistant to hydrolysis under the reaction conditions. For the preparation of 36 and 37, the heterooligomerization reaction conditions (3±24) are most successful because formaldehyde is neither added to the reaction mixture nor produced. The presence of free formaldehyde in the reaction mixture would otherwise trigger competitive hydroxymethylation of the N-atom of the amide. Alternatively, this problem circumvented by the use of secondary amines in the amidation reaction of $3_{ester}$ and $24_{ester}$ would lead to tertiary amide derivatives of 3 and 24 that would not be

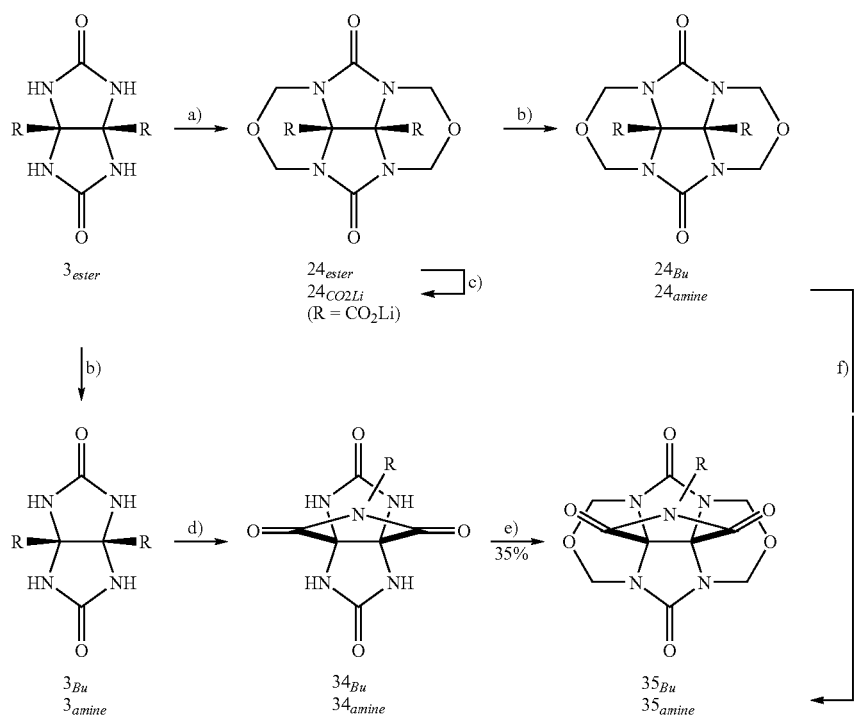

Scheme 7.

3 & 24: Bu (R = CONH(CH$_2$)$_3$CH$_3$); amine:(R = CONH(CH$_2$)$_3$N(CH$_3$)$_2$)
35: Bu (R = (CH$_2$)$_3$CH$_3$); amine:(R = (CH$_2$)$_3$N(CH$_3$)$_2$)

Conditions: a) TFA, (CH$_2$O)$_m$ 45%, b) neat amine, heat, >90%, c) MeOH, H$_2$O, LiOH, d) PTSA, ClCH$_2$CH$_2$Cl, heat, >90%, e) TFA, (CH$_2$O)$_m$ 35%, f) PTSA, ClCH$_2$CH$_2$Cl, 32%.

Thus, derivatives of CB[n] are prepared using the building blocks bearing electron withdrawing substituents described above. As in the synthesis of methylene bridged glycoluril dimers, there are three potential pathways to cucurbituril derivatives—two homomeric processes and one heteromeric pathway (Scheme 8). Preparation of 36-41 is effected by the classical CB[n] forming reaction under aq. acidic conditions (ex. 5 M HCl, or 9 M H$_2$DO$_4$) by the three pathways depicted in Scheme 8. We have already determined that $24_{ester}$ is not stable to aqueous reaction conditions because the esters undergo incomplete hydrolysis reactions. The diamides $3_{Bu}$, $3_{amine}$, $24_{Bu}$, and $24_{amine}$ and the imides $34_{Bu}$, $34_{amine}$, $35_{Bu}$, prone to hydroxymethylation or ring closure to the imides. The cyclization of the imdes 34 and 35 under both aqueous and anhydrous acidic conditions is facile as they neither undergo hydrolysis nor hydroxylmethylation reactions.

Purification of these reaction mixtures is performed as described above for unsubstituted CB[n]. In contrast to the other functionalized glycolurils, 34 and 35 are easily detected with handheld UV lamps at 254 mm, which facilitates chromatographic purification. In additional, the presence of the tertiary amine groups on $34_{amine}$ and $35_{amine}$ affords straightforward purification by ion-exchange chromatography on Dowex 50 since the number of basic N-atoms increases as ring size increases.

Scheme 8. Persubstituted Derivatives of CB[n].

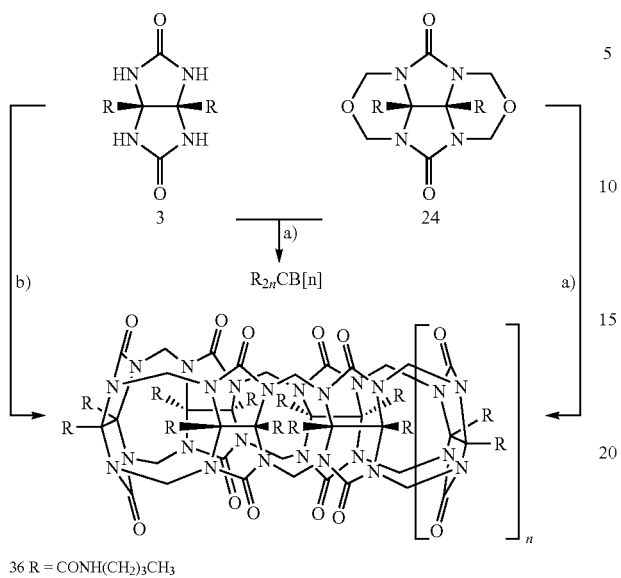

36 R = CONH(CH$_2$)$_3$CH$_3$
37 R = CONH(CH$_2$)$_3$N(CH$_3$)$_2$
38 R, R = (CO)$_2$N(CH$_2$)$_3$CH$_3$
39 R, R = (CO)$_2$N(CH$_2$)$_3$N(CH$_3$)$_2$
40 R = CO$_2$Et
41 R = CO$_2$H

Conditions: a) Aq. or anhydrous acid, b) Aq. or anhydrous acid, (CH$_2$O)$_n$.

D. Preparation of Glycoluril Monomer for the Synthesis of Persubstituted i-CB[n] Compounds and Derivatives Thereof The size distribution obtained in CB[n] syntheses under anhydrous conditions is linked to the length of the linear methylene bridged glycoluril oligomer formed. We describe herein methods for the selective preparation of CB[n] having specific values of n by a building block approach. For this purpose, we conducted the oligomerization reaction of $3_{ester}$ under anhydrous conditions (Scheme 9). We chose $3_{ester}$ for this demonstration since the formed oligomers have excellent CHCl$_3$ solubility which facilitated their purification and characterization. The major product of this reaction is the bis (cyclic ether) $24_{ester}$ along with smaller amounts of $42C_{ester}$ (10%), 42S, $43C_{3ester}$, 43SS, and 43CS. All five compounds are easily combination of selective extraction and recrystallization techniques.

Scheme 9. Synthesis of glycoluril oligomers.

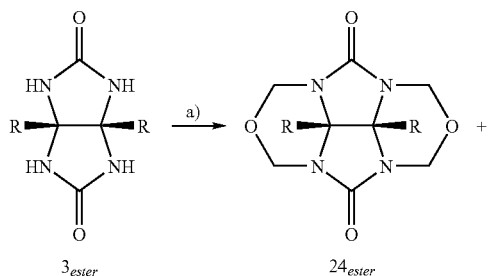

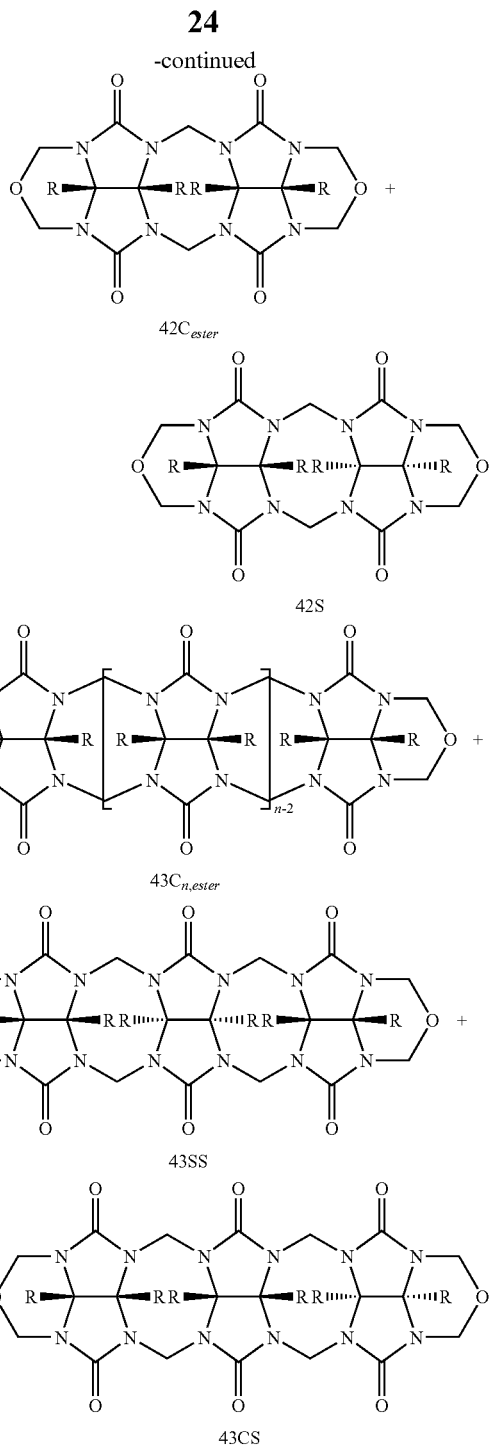

R = CO$_2$Et

Conditions: a) ClCH$_2$CH$_2$Cl, (CH$_2$O)$_n$, PTS, reflux.

Ureidyl NH terminated oligomers are conveniently used as components for tailor-made CB[n] formation. As in the case of the dimerization reactions (Scheme 8), there are three potential routes to CB[n] and derivatives—those involving homo-oligomerization of glycoluril derivatives (3) or cyclic ethers (24) and hetero-oligomerizations of 3 and 24. For this latter purpose, we prepared methylene bridged glycoluril oligomers that have free ureidyl NH groups at their termini. Treatment of $42C_{ester}$ with 3,5-dimethylphenol in TFA resulted in a methylene group transfer reaction yielding deprotected 44C$_{ester}$ in 59% yield (Scheme 14).

Because the S- to C-shaped isomerization is an intramolecular process under anhydrous conditions, reaction of dimeric building block 42C selectively afford R$_{2n}$ (CB[n] 40 (Scheme 15) with values of n divisible by 2 (n=6, 8, 10, etc.). Similarly, we believe that methylene bridged glycoluril timer 43C$_{3,ester}$, will yield mainly 40 with values of n that are divisible by three (n=6, 9, 12, etc.). To selectively access larger CB[n] derivatives in the manner, one may use 44C$_{4,ester}$, for example, as a starting material. Alternative, the highly selective heterodimerization reaction reported above (Scheme 8) is an alternative. For example, a combination of 42C$_{ester}$ and 44C$_{ester}$ affords a mixture of CB[n] derivatives where n is a multiple of four (n=8, 12, 16, etc.). Similarly, reaction of 42C$_{ester}$ and 45C$_{3,ester}$ affords a mixture of CB[n] derivatives where n is a multiple of five (n=5, 10, 15, etc.). These synthetic sequences offer more control that traditional CB[n] forming reactions. Numerous variations of these two themes are possible using oligomers of different lengths that bear diverse functional groups.

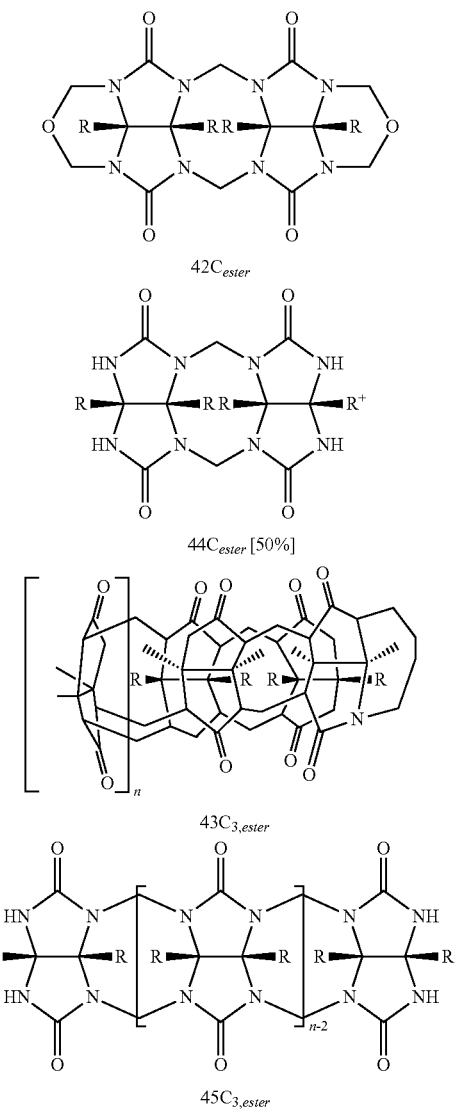

⑦ indicates text missing or illegible when filed

We also describe herein the synthesis of cucurbituril derivatives incorporating one or more aromatic rings into their structure. Such compounds, as a result of their potentially functionalizable sites along their rims offer opportunities that CB[n] derivatives functionalized along their equator described above do not. Such compounds, for example, are linked end-to-end to form rigid rod tubular structures that could be useful as transmembrance channels, nanoscale probes, or chemical sensors. In addition, the presence of aromatic rings eliminates the putative 1,5-diaxial interactions that potentially restrict access to larger CB[n] derivatives. Thus, we present two complementary strategies toward the synthesis of CB[n] analogs with aromatic rings in the CB[n] framework.

The use of aromatic rings to reduce or avoid 1,5-diaxial interactions, thus, allows in a straightforward manner the synthesis of large ring CB[n] and i-CB[n] compounds.

Hydrazides function as nucleophilic glycoluril substitutes in typical methylene bridge forming reactions. We hypothesized that molecules with nucleophilic N-atoms might serve as glycoluril surrogates in CB[n] forming reactions. We discovered that acylhydrazides 50 and 51 undergo extremely repaid reaction with 52 and 42C$_{ester}$ yielding 53 and 54, respectively (Scheme 18). In these reactions, we do not observe reactions resulting from the self-condensation of the cyclic ethers 52 and 42C$_{ester}$. The cause of the enhanced reactivity of 50 and 51 can be ascribed to the a-effect—the neighboring N-atom enhances its nucleophilicity.

This reaction may also be extended to the use of bis(hydrazides) 55 and 56 to allow for the formulation of CB[n] derivatives incorporating one or more hydrazide units. These bis(hydrazides) combine several attractive features: 1) they are highly reactive and serve as excellent heterodimerization partners, 2) their connection to the glycoluril units should be susceptible to the same S- to C-shaped isomerization as glycoluril dimers, 3) they have no steric bulk on their external face facilitates the preparation of the larger CB[n] derivatives, and 4) since the lengths of 55 and 56 are different than that of glycoluril, the size, number, and substitution pattern of the formed CB[n] derivatives will be governed by whether these lengths are commensurate or incommensurate. The co-heterooligomerization of suitably selected compounds along the above lines will yield trisubstituted CB[6] and tetrasubstituted CB[8] analogs analogs, for example.

Scheme 18. Surrogates for glycoluril in CB[n] formation.

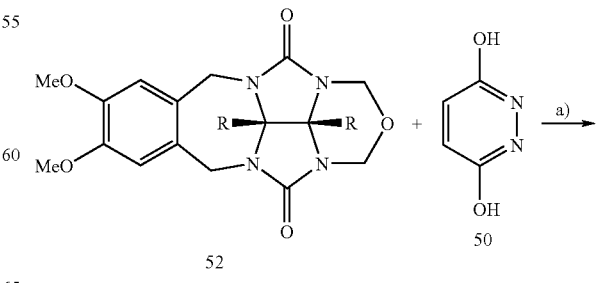

R = CO$_2$Et

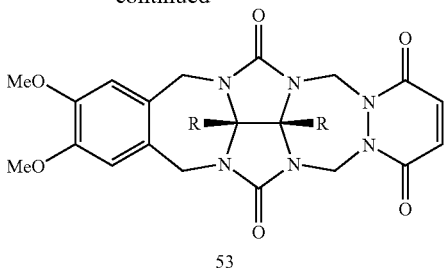

53
R = CO₂Et

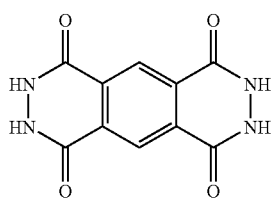

55

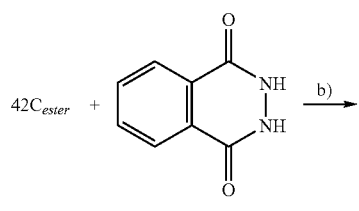

51

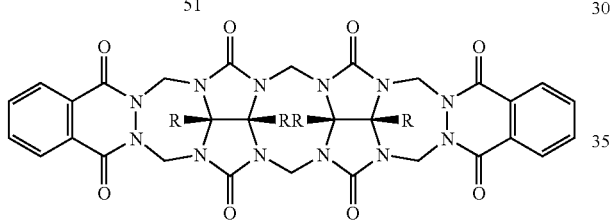

54
R = CO₂Et

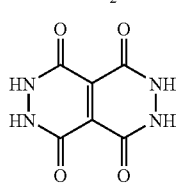

56

Conditions: a) TFA, reflux, 55%, b) PTSA, ClCH₂CH₂Cl, reflux, 71%.

Thus, generally in accordance with the present invention paraformaldehyde is reacted with one or more compounds capable of reacting therewith to form methylene bridges. Examples of such compounds are glycolurils, glycoluril cyclic ethers or arylhydrazines, such as phenylhydrazide or toluoylhydrazide.

Further, as noted above, if glycolurils or glycoluril cyclic ethers are used, it is preferred that they bear an electron-withdrawing carboxylic acid moiety, such as lower alkyl carboxy, i.e., —CO₂Me or —Co₂Et.

Additionally, the solvent may either be acidic aqueous or acidic anhydrous in nature. Acids generally used are TFA, PTSA or MeSO₃H. Examples of anhydrous solvents are hydrocarbons, or chlorinated hydrocarbons, for example. The term "anhydrous" generally means the organic solvent contains less than 0.01% by wt. of water, and preferably less than 0.001% by wt. of water. Organic solvents used may be dried using any conventional drying agent which are well known to those skilled in the art.

The present invention will now be further defined by reference to certain Examples which are provided solely for purposes of illustration and are not intended to be limitative.

Example 1

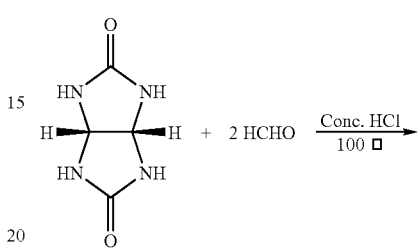

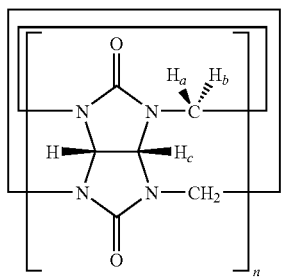

CB[5]
CB[6]
Introverted CB[6]
CB[7]
CB[8]
CB[5] @ CB[10]
Introverted CB[7]

Synthesis:

Powered glycoluril (795 g, 5.59 mol) and powered paraformaldehyde (354 g, 11.20 mmol) were mixed thoroughly. An ice-cold concentrated HCl solution (1130 mL) was added gradually while stirring with a large glass rod. After the addition of a ~100 m/, stirring was no longer possible and solidification was observed and an exotherm was observed. The heterogenous mixture was gradually heated to 80□ (2.5 h) and maintained at that temperature for 2.5 hours until all the solid had dissolved. The homogenous red solution was heated to 100° C. for 14 hours. After cooling to room temperature, the purification process was begun.

Purification:

Initial processing: The reaction mixture which contains a large amount of solid was evaporated as to a minimum volume. This slurry was poured into water (2.5 L). The solid was collected by filtration to give the first crop (Crop I) (contains: CB[6], CB[7], CB[8], some introverted CB[6], and some CB[5]@CB[10]). The filtrate was evaporated to about 600 mL and then slowly poured into a mixture of MeOH (3 L) and water (200 mL) with vigorous stirring. After stirring overnight, the precipitate was obtained by filtration to give a second crop (Crop 2 contains: CB[7], CB[6], and CB[5]).

Subsequent Purification: Overview

The separation of each component (CB[5], CB[6], CB[7], CB[8], CB[5]@CB[10], and introverted CB[6]) from Crop 1 and Crop 2 was effected due to their differential solubility in HCl solutions.

CB[5]. CB[5] and CB[7] have moderate solubility in water but other CB[n] almost are insoluble in water. By washing the crude solids repeatedly with large volumes of water a mixture of CB[5] and CB[7] was isolated. Separation of CB[5] from CB[7] is based on its moderate solubility (about 33 mg/mL) in 50% aqueous MeOH solution (v/v). The solubility of CB[7] is less than 4 mg/mL in this solution. By extracting the solid mixture of CB[5] and CB[7] with 50% aq. MeOH CB[5] is separated from CB[7].

CB[8]. CB[6], introverted CB[6], and CB[5]@CB[10] have appreciable solubility in 3 M HCl solution whereas CB[8] is substantially less soluble. By washing the crude mixture of CB[6], CB[8], CB[5]@CB[10], introverted CB[6], and CB[8] with 3 M HCl CB[8] is isolated as an insoluble solid.

CB[5]@CB10. CB[6], introverted CB[6], and CB[5]@CB[10] were separated by fractional crystallization from different concentration HCl solutions. CB[5]@CB[10] was crystallized from the mixture by using concentrated HCl as solvent.

Introverted CB[6]. Introverted CB[6] is less soluble than CB[6] in 0.2 M aq. $Na_2SO_4$ which allows it to be isolated as an insoluble solid by washing and filtration.

Introverted CB[7] is readily separable from introverted CB[6] by gel permeation chromatography (GPC).

Final Purification:

CB[5] was recrystallized from water (8% yield).

CB[6] was recrystallized from concentrated HCl solution (50% yield).

Traces of CB[6] can be removed from Introverted CB[6] by the addition of water to an HCl solution of the mixture containing 1,6-diaminohexane. The solid introverted CB[6] is recrystallized by diffusing water into its HCl solution to yield the pure form (2% yield).

CB[7] was washed many times using 50% methanol aqueous solution (v/v). Diffusion of acetone into an aqueous solution of CB[7] gave a crystalline solid (25%).

CB[8] was recrystallized from concentrated HCl solution (10% yield).

CB[5]@CB[10} was recrystallized from concentrated HCl solution (2% yield).

Example 2

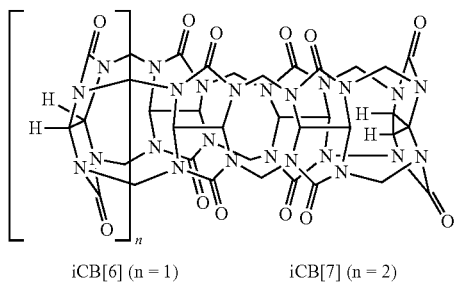

iCB[6] (n = 1)        iCB[7] (n = 2)

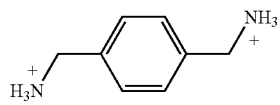

1

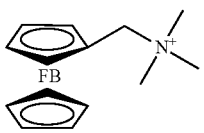

2

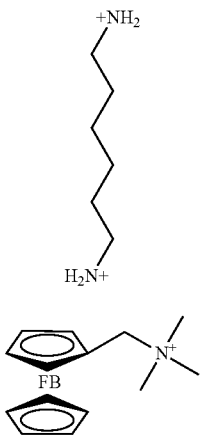

3 i-CB[6] and i-CB[7] were synthesized using the procedures described above. Each were characterized by $^1$H NMR spectroscopy and x-ray crystallography, after separation by gel permeation chromatography.

Figure 4:
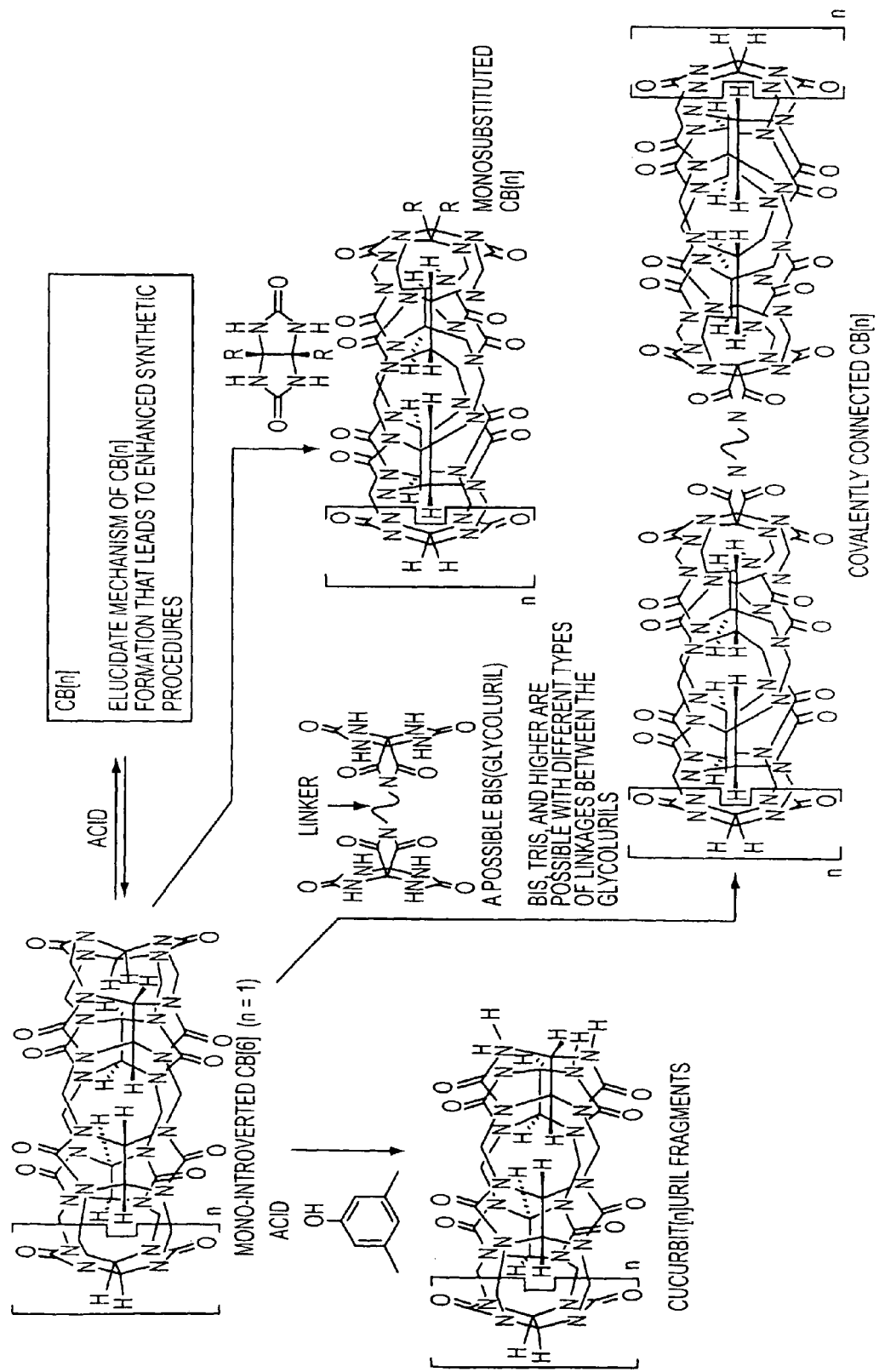
FIG. 4 illustrates $^1$HNMR spectra recorded with water presaturation for: a) mixture of i-CB[6] ● 1(●), i-CB[7] 0.1 (◆), CB[7] 0.1 (◇), and CB[6] 0.1 (○), b) i-CB[6], c) i-CB [7] (500 MHz), $D_2O$:NaCl, 298K.
Figure 6:
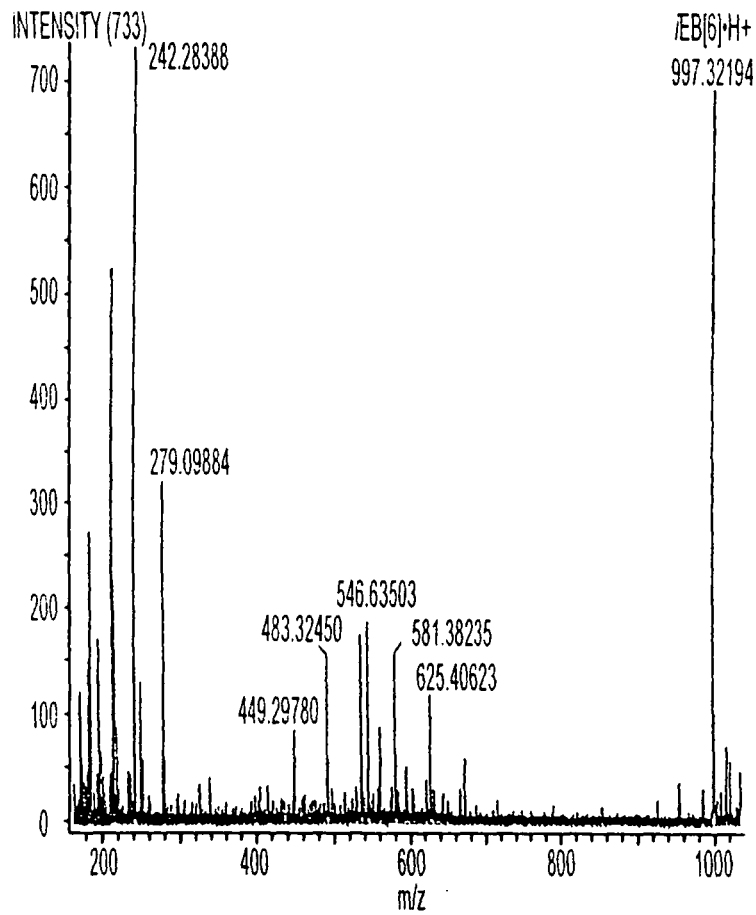
FIG. 6 illustrates $^1$HNMR spectra recorded for: a)) i-CB[6], CB[6] and 1 in a ratio of 1:1:2 (0.5M NaCl), and b) i-CB[7], 1 and 2 in a ratio of 1:1:1 (500 MHz, $D_2O$), RT).
Figure 7A:
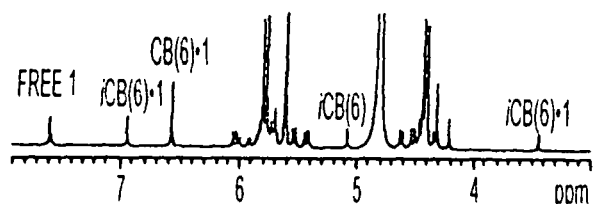
FIG. 7 illustrates a ES-MS spectrum of i-CB[6].
Figure 7B:
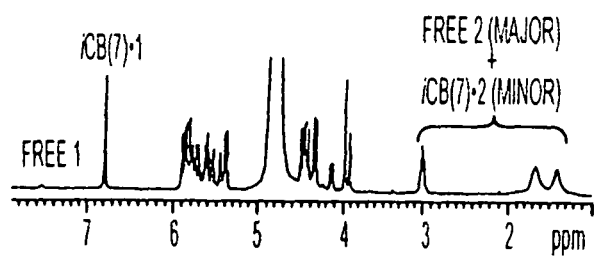
Figure 8:
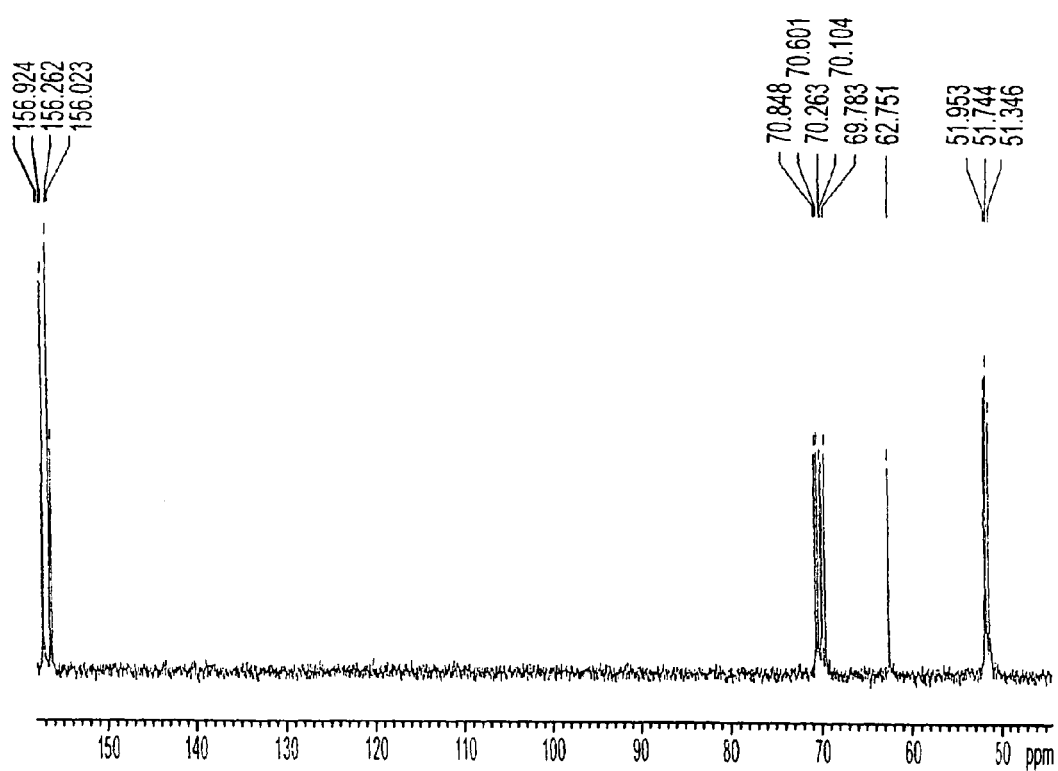
FIG. 8 illustrates a $^{13}$CNMR spectrum of i-CB[6] (400 MHz, $D_2O$/DC1).
Figure 9:
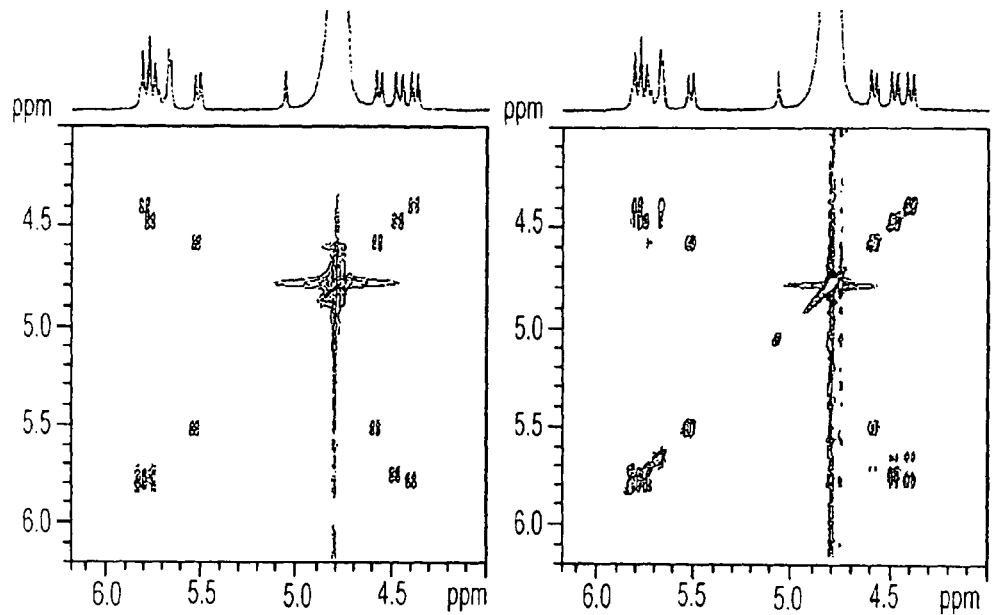
FIG. 9 illustrates DQF-COSY and ROESY spectra of i-CB[6].
Figure 10A:
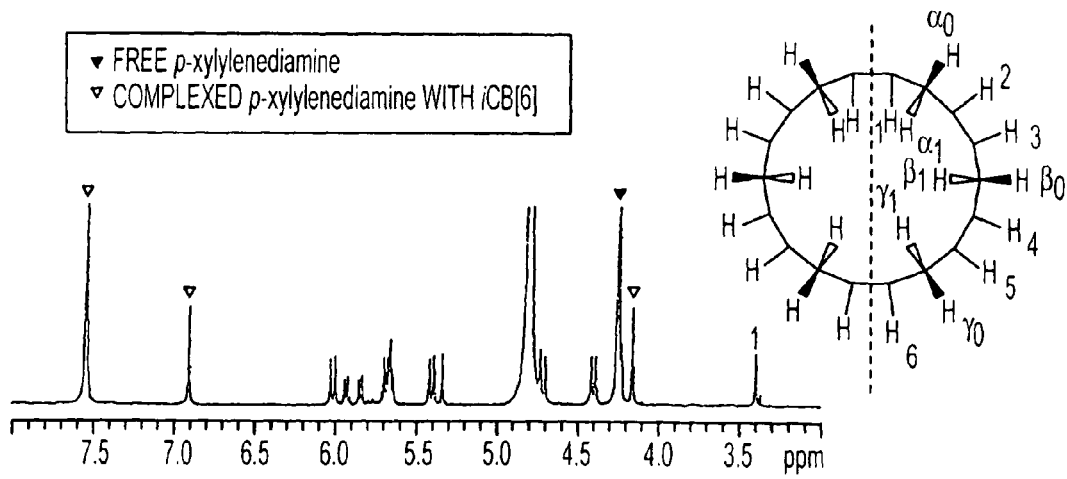
FIG. 10 illustrates $^1$HNMR spectra of i-CB[6] complexed with 1.
Figure 10B:
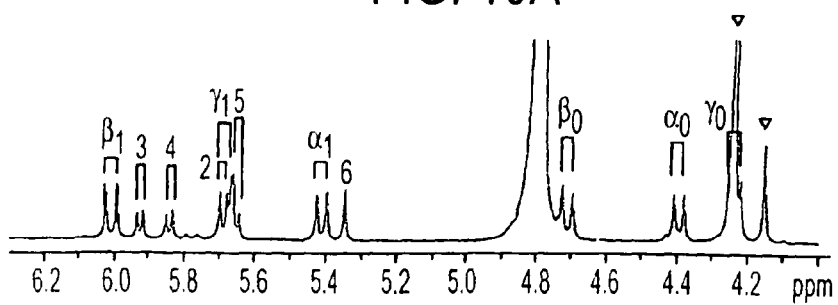
Figure 11:
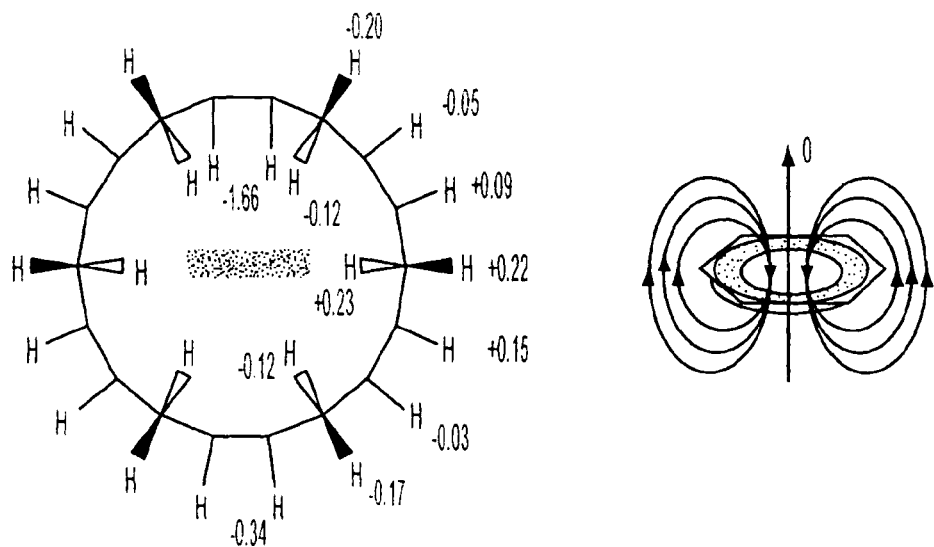
FIG. 11 illustrates complexation induced shifts of i-CB[6] protons upon complexation with 1.
Figure 12:
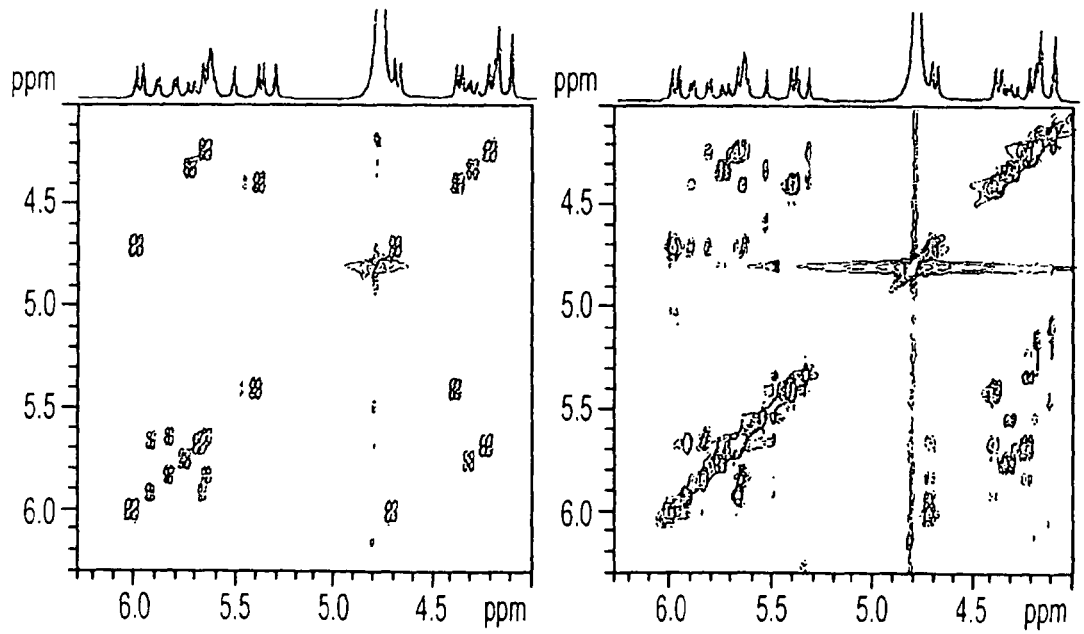
FIG. 12 illustrates DQF-COSY and ROESY spectra of i-CB[6] ●1.
Figure 13:
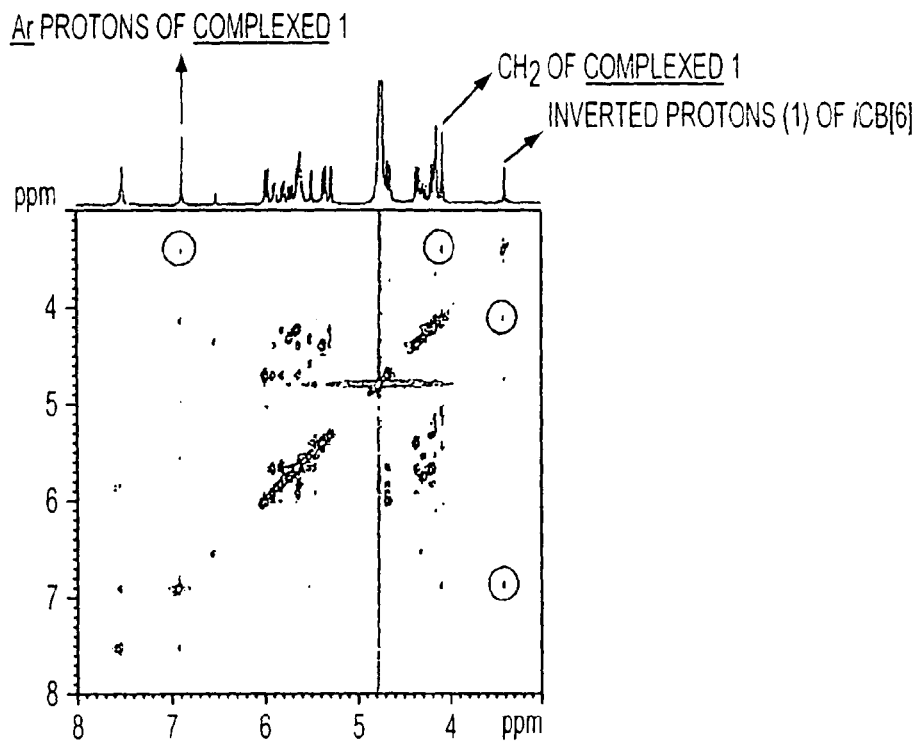
FIG. 13 illustrates intermolecular NOEs between i-CB[6] and I in i-CB[6] ●1.
Figure 14:
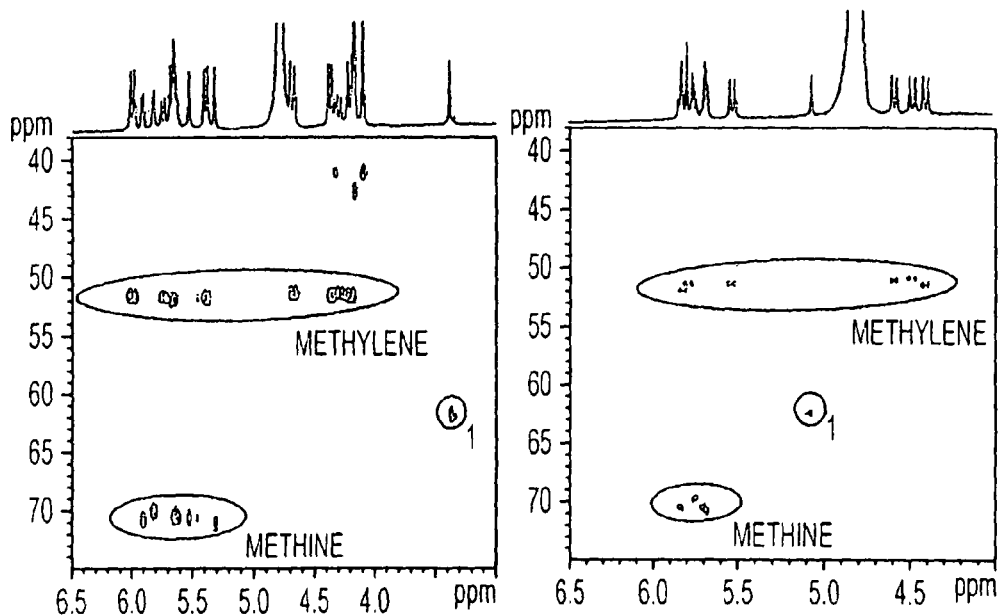
FIG. 14 illustrates $^1$H—$^{13}$C HSQC spectra of i-CB[6] ●1 and i-CB[6].
Figure 15:
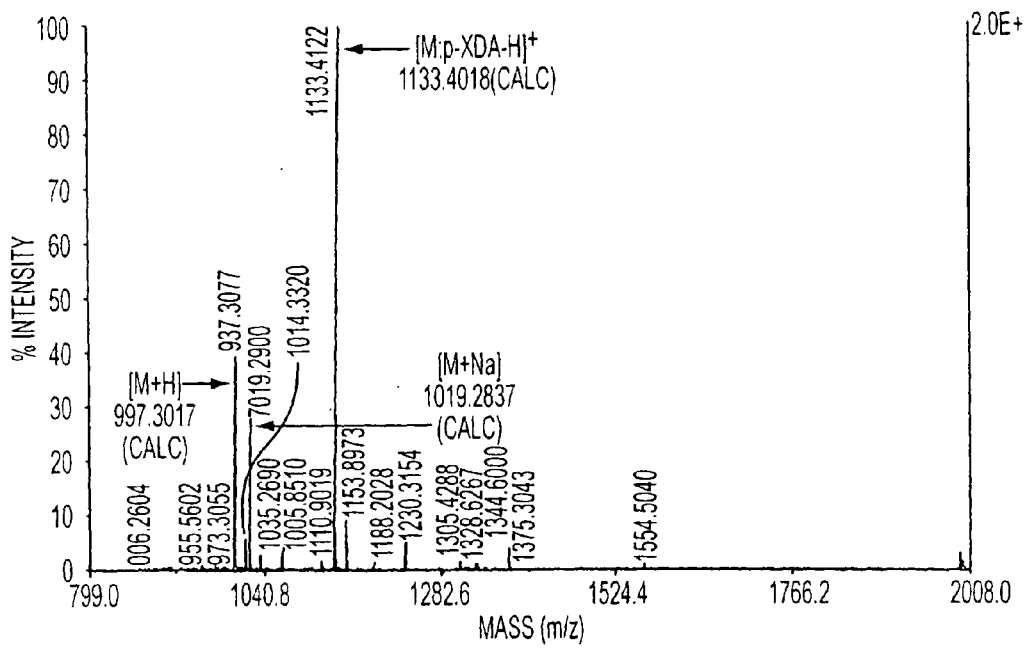
FIG. 15 illustrates MALDI-TOF spectrum of i-CB[6] ●1.
Figure 16:
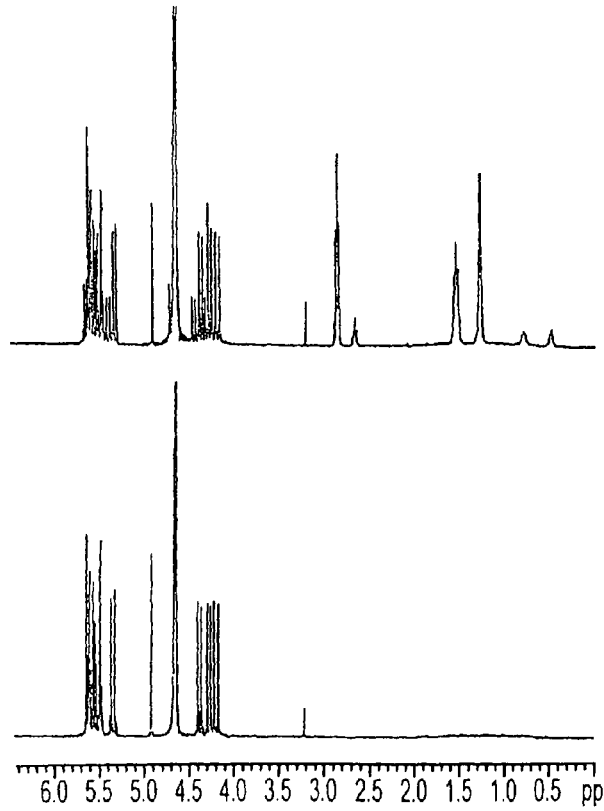
FIG. 16 illustrates $^1$HNMR spectra for i-CB[6] above (bottom) and with excess 1,6-hexane diamine (tsp).
Figure 17:
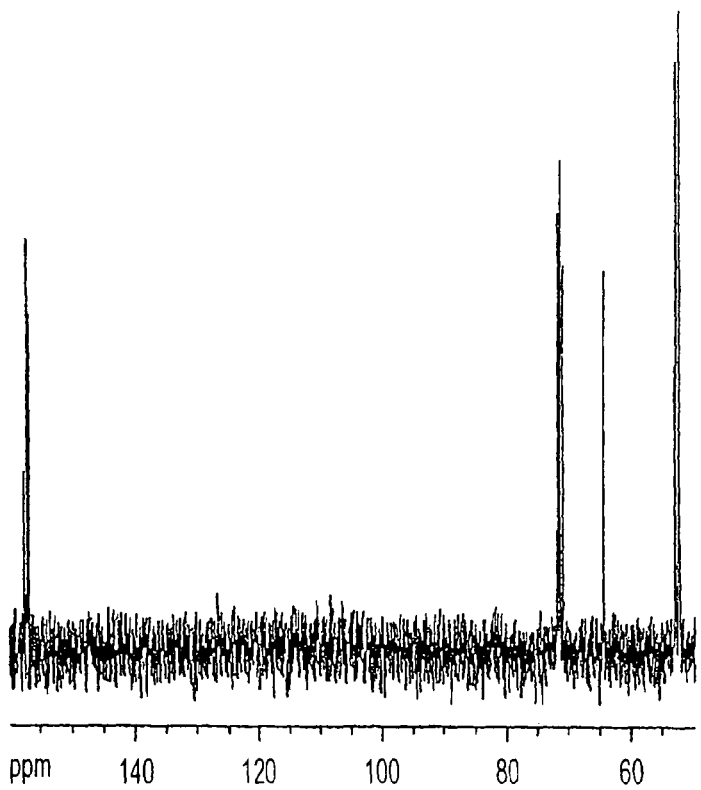
FIG. 17 illustrates a $^{13}$CNMR spectrum for i-CB[7] (125 MHz, $D_2O$).
Figure 18:
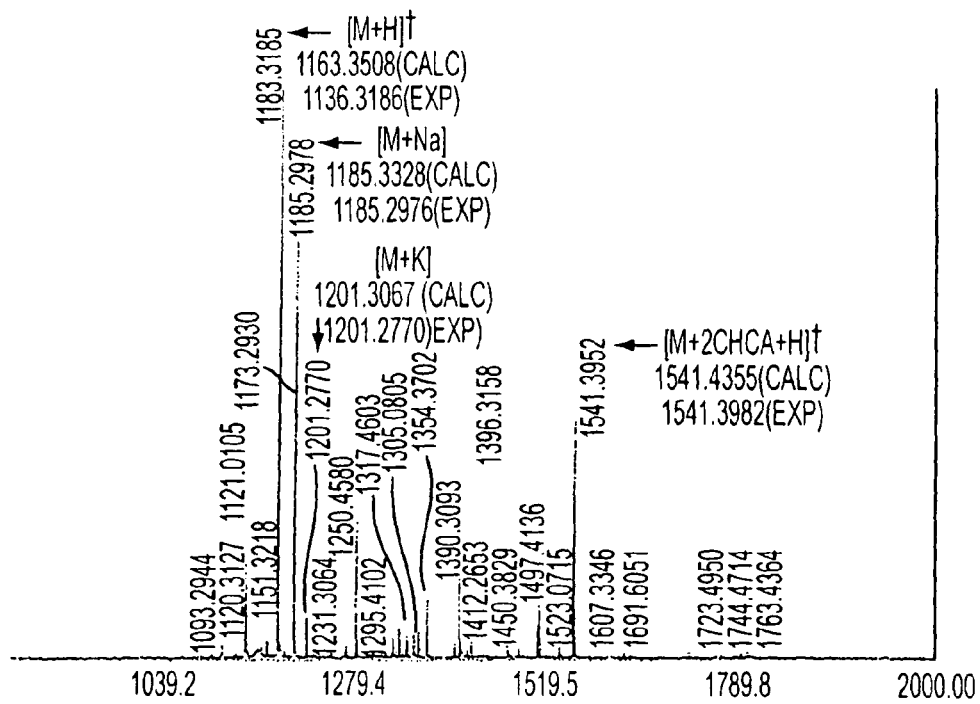
FIG. 18 illustrates MALDI-TOF spectrum of i-CB[7].
Figure 19:
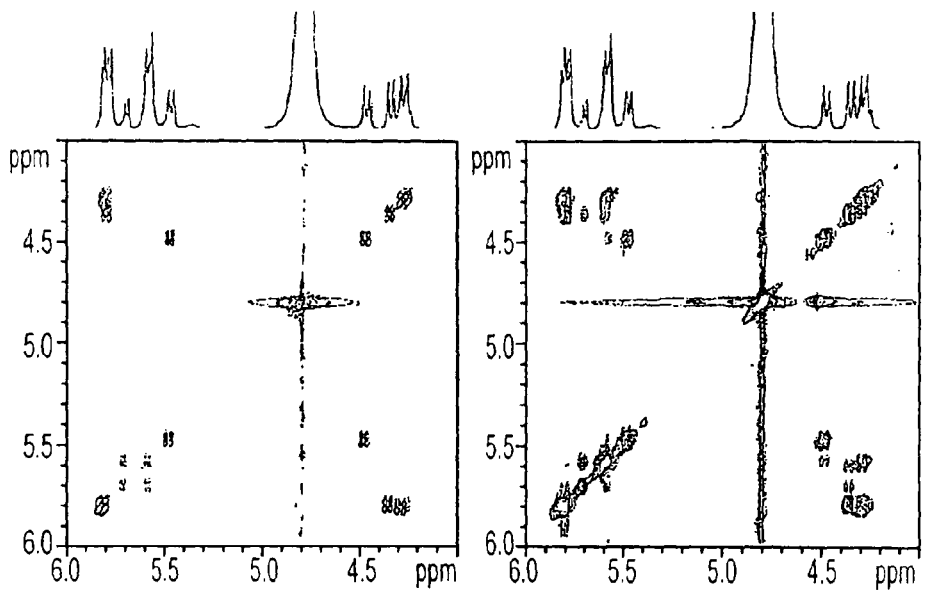
FIG. 19 illustrates DQF-COSY and ROESY spectra of i-CB[7].
Figure 20:
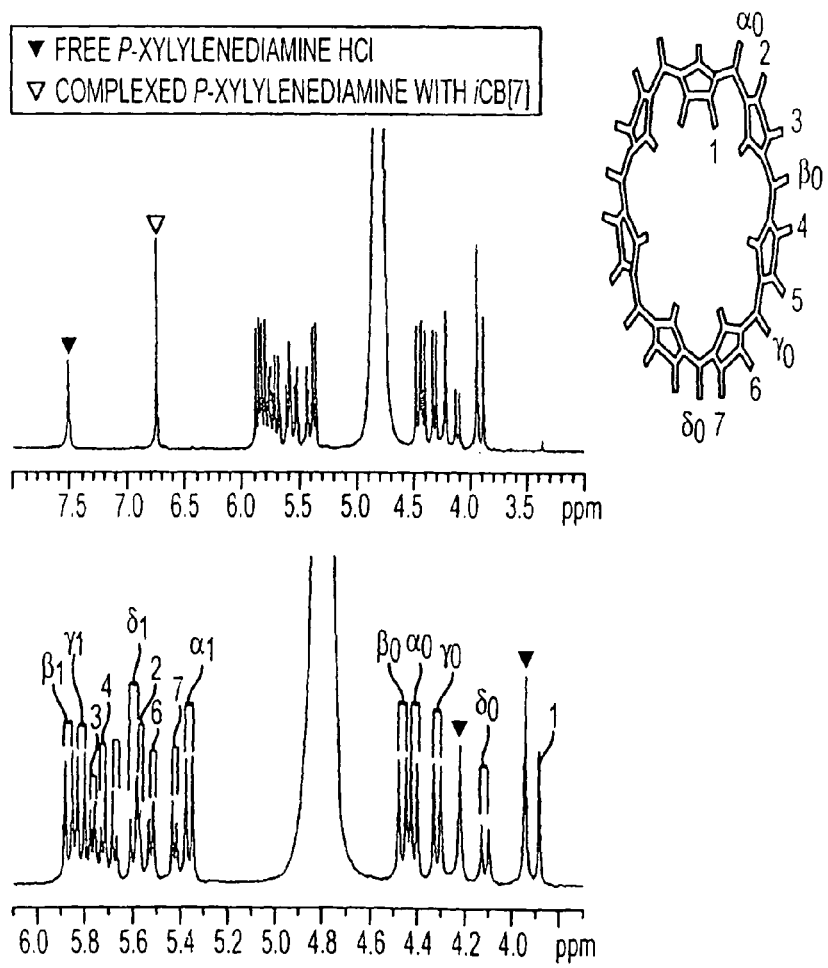
FIG. 20 illustrates $^1$HNMR spectrum of i-CB[7] ●1.
Figure 21:
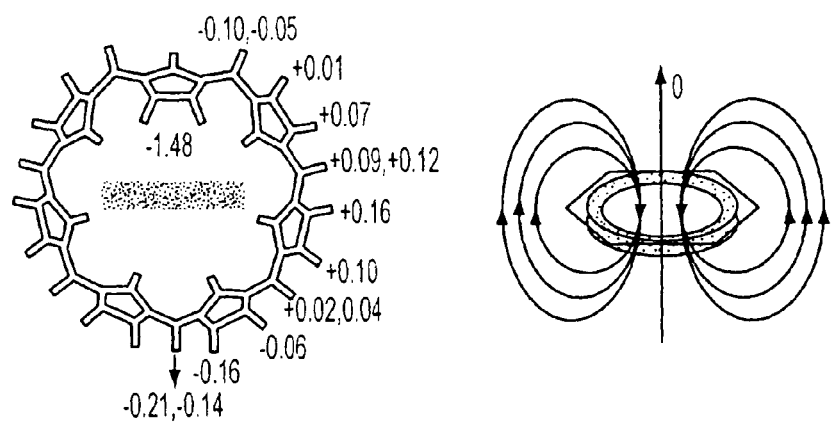
FIG. 21 illustrates complexation induced shifts of i-CB[7] protons upon complexation with 1.
Figure 22:
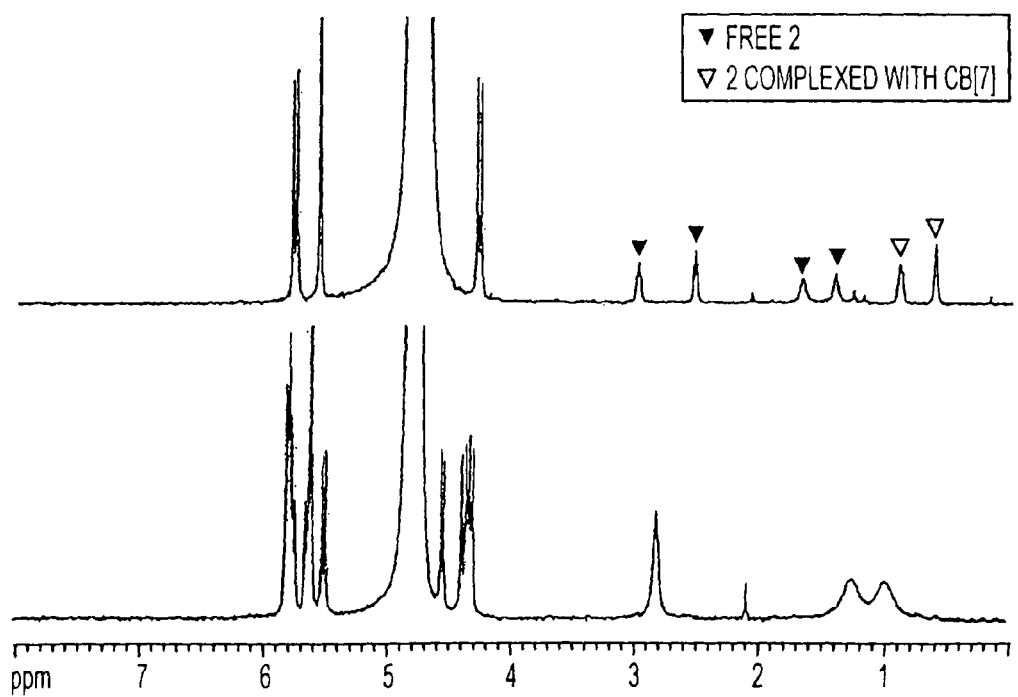
FIG. 22 illustrates $^1$HNMR spectra of CB[7] (top) and i-CB[7] (bottom) with a slight excess of 2. In the presence of CB[7] (top), there are two sets of NMR signals corresponding to free 2 and complexed 2 with CB[7].
Figure 23:
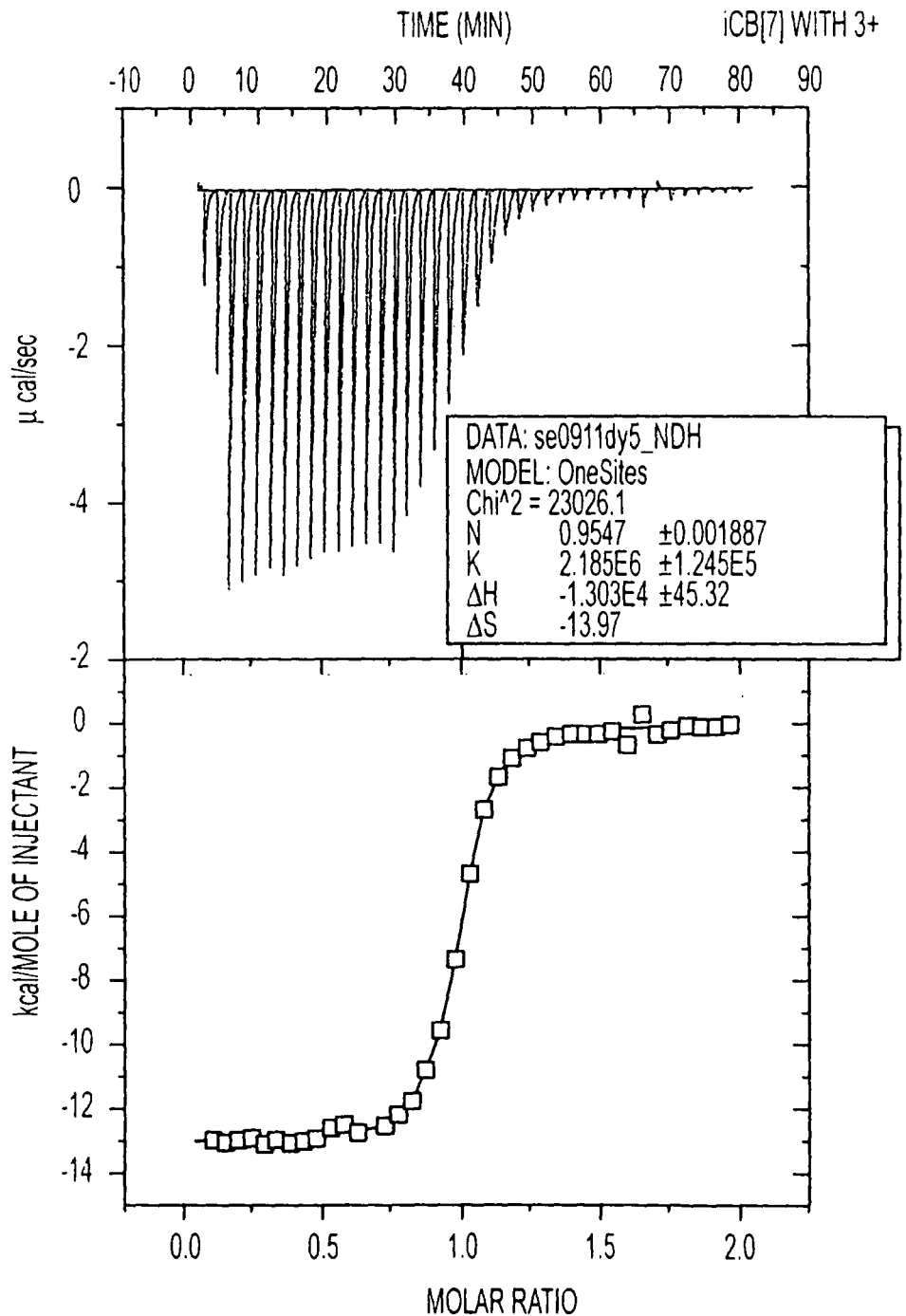
FIG. 23 is a thermogram (top) and binding isotherm (bottom) of (ferrocenemethyl) trimethyl ammonium in complexing with i-CB[7] at 303K.

The i-CB[n] are detected by $^1$H NMR spectroscopy in CB[n] reaction mixtures produced from the reaction between glycoluril and formaldehyde in acidic media. When p-xylylenediammonium ion (1) is added as a probe to a mixture of CB[n], each different CB[n]⊙1 and i-CB[n]●1 exhibits a single diagnostic aromatic resonance (FIG. 4a, 6.9-6.4 ppm). i-CB[6] and i-CB[7] were isolated in 2.0% and 0.4% yields, respectively, in pure form either by gel permeation chromatography (Superdex 30, 0.15 M $NH_4HCO_3$) or by fractional crystallization (18% aq. HCl) followed by selective complexation (i-CB[6]: $^+H_3N(CH_2)_6NH_3^+$, 2) to remove other CB[n]. The structures of i-CB[6] and i-CB[7] (FIGS. 4b and 4c) were unequivocally established by 2D NMR spectroscopy.

The methane resonances for the inverted subunit of i-CB[6] appear as small but distinct signals at ~5.05 ppm and 62.8 ppm in open regions of the $^1$H and $^{13}$C NMR spectra, respectively, which are upfield-shifted compared with those of CB[6] (5.65 and 71.0 ppm, respectively). The inverted protons of i-CB[6] and i-CB[7] undergo remarkable upfield shifts (1.66 and 1.48 ppm. respectively) when complexed to 1 due to the anisotropic effect of the aromatic ring of 1 as well as its preferred alignment along the long axis of the i-CB.

Figure 5:
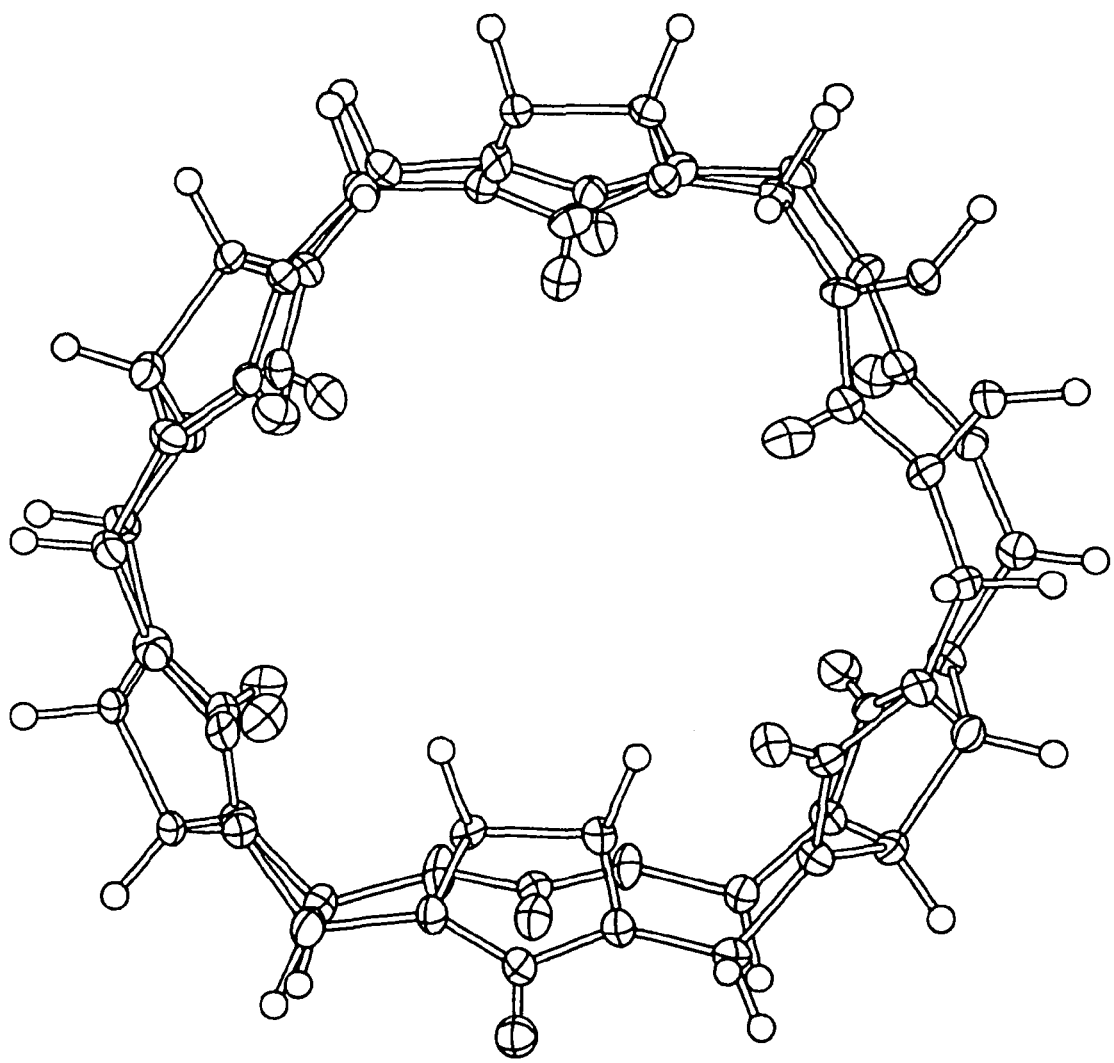
FIG. 5 depicts a view of introverted CB[6] from crystal structure data.

We obtained single crystals of i-CB[6] and i-CB[7] that were suitable for structure determination by x-ray diffraction. FIG. 5 shows their X-ray crystal structures. The most striking feature is the inverted glycoluril unit which places two methane portons within the cavity. This inverted glycoluril unit decreases the cavity volume of i-CB[n] relative to their CB[n] counterparts., flattens the inner surface of the macrocycle, alters the electrostatic potential within the cavity, and displays two ureidyl-carbonyl groups outward which gives the macrocycle a permanent dipole moment (AM1: μ=10.63 S NS 9.77 D fpr i-CB[6] and i-CB[7], respectively.

Because of their smaller cavities and more open portals i-CB[6] and i-CB[7] bind most guest molecules less tightly than their CB[n] counterparts do. For example, when a light excess of 1 is added to a solution containing CB[6] and i-CB[6] (1:1), almost all CB[6] forms a complex with the guest, but only a half of i-CB[6] does so as shown in FIG. 3a. Alkyl ammonium ions such as 2 are known to bind tightly to CB[6] with values of $K_a$ in the μM range. In contrast, 2 bind less strongly to i-CB[6] (i-CB[6]●2: $K_a$=460±50 $M^{-1}$ in 0.1 M $Na_2SO_4$). Similarly, i-CB[7] retains the ability to bind to guests commonly bound to CB[7]1,8 (e.g. 1.2, and (ferrocenemethyl)trimethylammonium ion (3)) but with lower affinity and higher kinetic liability. The association constants (Ka) for the guests 1, 2, and 3 with i-CB[7] measured by isothermal titration calorimetry (ITC) are $(9\pm1)\times10^6$ M$^{-1}$, $(8.8\pm0.9)\times10^5$ M$^{-1}$, and $(2.2\pm0.1)\times10^6$ M$^{-1}$, respectively, which are 2 to 6 order of magnitude lower than those with CB[7].

Interestingly, however, i-CB[6] and i-CB[7] show a distinct preference for guests with a flatter profile. For example, i-CB[7] binds aromatic guest 1 more strongly than linear aliphatic guest 2. In the presence of 1 equiv 1 and 2, the majority of i-CB[7] forms a complex with 1, while 2 exists mainly as a free guest. Also the $K_a$ value of i-CB[7] for 1 higher than that for voluminous guest 3, which is in sharp contrast to the behavior of CB[7] which displays much high affinity for 3 than 1. Thus, the inverted glycoluril unit modulates guest binding affinity and rates of dissociation, both of which are of critical importance in the creation of CB[n] based molecular machines.

To determine whether i-CB[6] and i-CB[7] are kinetic or thermodynamic products in CB[n] forming reactions product resubmission experiments were conducted. When purified i-CB[6] was heated in conc. DC1 lit was transformed into a mixture of CB[5], CB[6], and CB[7] (24:13:1) in 87% combined isolated yield. When i-CB[7] was treated similarly a 4:1 mixture of CB[6], and CB[7] was obtained in 71% combined yield. These results allow us to add a new complexity to the currently accepted mechanism of CB[n] formulation—namely that i-CB[n] are viable intermediates.

Experimental Section: Detailed Procedures

General. The guests used in this study were purchased from commercial suppliers and were used without further purification. The crude cucurbit[n]uril (CB[n]) mixture was preferred according to the literature procedures. Gel permeation chromatograph was performed using Sephadex G-15 or Superdex 30. Melting points were measured on a Meltemp apparatus in open capillary tubes and are uncorrected. IR spectra were recorded on a Nicolet Magna or on a Perkin Elmer Spectrum GX FT-IR spectrophotometers as KBr pellets and are reported in cm$^{-1}$. NMR spectra were measured on a Bruker AM400 or on a Bruker DRX500 spectrometers operating at 400 or 500 MHz for $^1$H and 100 or 125 MHz for $^{13}$C. 2D NMR experiments were performed using the standard pulse sequences supplied by the manufacturer. Mass spectrometry was performed on a JEOL AccuTOF electrospray instrument, or on an ABI 4700 Proteomics Analyzer MALDI-TOF instrument. The formation constants for the inclusion of several guests in iCB[7] were determined by isothermal titration calorimetry using a VP-ITC instrument from MicroCal. All solutions were prepared in purified water (Milli-Q, Millipore). A solution (0.2 mM) of iCB[7] was placed in the sample cell. As 5 mM solution of guests was added in a series of fifty injections (4 μL), the heat evolved was recorded at 30° C.

Purification of iCB[6] Fractional Recrystallization. A crude CB[n] reaction mixture prepared from 80 g of glycoluril by the literature method was used in subsequent purification steps.

In processing. The reaction mixture which contains a large amount of solid was evaporated to a minimum volume. This slurry was poured into water (250 mL). The solid was collected by filtration to give the first crop (Crop 1) (contains: CB[6], CB[7], Cb[8], and some iCB[6]). The filtrate was evaporated to about 60 mL and then slowly pored into a mixture of MeOH (300 mL) and water (20 mL) with vigorous stirring. After stirring overnight, the precipitate was obtained by filtration to give a second crop (Crop 2 contains CB[7], CB[6], and CB[5]).

Subsequent purification. The separation of each component (CB[5], CB[6], CB[7], CB[8], and iCB[6]) from Crop 1 and Crop 2 was enabled due to their differential solubility in HCl solutions.

CB[5] and CB[7]. CB[5] and CB[7] were isolated in pure from using the literature procedure[1] which relies on the solubility of both CB[5] and CB[7] in water and the moderate solubility of CB[5] in 50% aqueous MeOH (v/v).

CB[8]. CB[6] and iCB[6] have appreciable solubility in 3.5 M HCl solution whereas CB[8] is substantially less soluble. By washing the crude mixture of CB[6], Cb[8], and iCB[6] with 3.5 M HCl it is possible to isolate Cb[8] as an insoluble solid.

iCB[6] and CB[6]. CB[6] and iCB[6] were separated by fractional crystallization from different concentration HCl solutions. For example, the initial CB[6]/iCB[6] mixture was recrystallized from a minimum volume of conc. HCl. The filtrate is enriched in iCB[n]; adding the filtrate to MeOH gives the precipitate which is filtered and dried. The solid now enriched in iCB[6] is recrystallized from 17.5% HCl which gives CB[6] as a solid and filtrate further enriched in iCB[6]. In this manner, the ratio of iCB[6]:CB[6] is raised to ≈80:20. At this point, the mixture is dissolved in a minimum of conc. HCl. To this solution is added enough $H_2N(CH_2)_6NH_2$ to complex all of the CB[6] (≈25%). This solution is then diluted 5-fold with $H_2O$. The precipitate is isolated by centrifugation and washed several times with $H_2O$ which yields iCB[6] as a white solid in 2% overall yield.

Purification of iCB[7] by Gel Permeation Chromatography.

Initial processing. A partially purified CB[n] mixture (20 g) was stirred in aqueous 0.15 M $NH_4HCO_3$ solution (500 mL) for 3 h. The insoluble solid (mostly CB[6] and iCB[6] (~86%, 5:4), and some CB[8] (7%)) was filtered off, and methanol (1 L) was added in small portions to the filtrate. The fine precipitate was collected by filtration to give the first crop (contains: CB[7], iCB[7] (~94%, 4:1), and some CB [6] and iCB[6] (~6%)). This procedures was repeated once to enrich the solid in iCB[7] (up to CB[7]: iCB[7]≈3.2).

Purification of iCB[7] by GPC. A sample enriched in iCB[7] (~g) dissolved in 10 mL of 0.15 M $NH_4HCO_3$ solution was injected on a Superdex™ 30 column (HiLoad™ Prep Grade, 26×600 mm). Elution with 0.15 M $NH_4HCO_3$ solution of flow rate of 2 mL/min., while monitoring at 184 nm, provided baseline separation between CB[7] (retention volume, $R_v$=270-530 mL) and iCB[7] ($R_v$=600~890 mL). After evaluating the purity of selected fractions by $^1$H NMR spectra, fractions ere combined and lyophilized to obtain pure iCB[7] (69 mg).

Characterization of iCB[6] and iCB[7].

iCB[6]. White solid. M.p.>300° C. IR (KBr, cm$^{-1}$): 3446s, 2994w, 2927w, 2850w, 1735s, 1478s, 1417m, 1377m, 1328m, 1238s, 1192m, 966m, 803s. $^1$H NMR (400 MHz, 35% DCl/$D_2O$): 5.60 (d, J=8.5, 2H), 5.48 (d, J=8.5, 2H), 4.50-4.45 (ABq, 4H) 5.42 (s, 2H), 5.32 (d, J=15.7, 4H), 5.30 (d, J=15.7, 4H), 5.13 (d, J=14.0, 4H), 5.02 (s, 2H) 4.34 (d, J=14.0 4H), 4.32 (d, J=15.7, 4H), 4.20 (d, J=15.7 4H) $^{13}$C NMR (100 MHz, 35% DCl/$D_2O$): 157.1, 156.9, 156.3, 156.0, 70.9, 70.6, 70.3, 70.1, 69.8, 52.0, 51.7, 51.4. MS (ES): m/z 997 (100, [M+H]$^+$). HR-MS (ES): m/z 997.3219 ([M+H]+, $C_{36}H_{37}N_{24}O_{12}$, calcd 997.3023). Anal. Calcd for $C_{36}H_{36}N_{24}O_{12}\cdot(H_2O)_6$: C 39.13, H 4.37, N 30.42. Found: C 39.38, H 4.38, N 30.24.

iCB[7]. White solid. M.p. 300° C. IR (KBr, cm$^{-1}$): 3445s, 2994w, 2928w 1734s, 1474s 1420m, 1377m, 1325m, 1233m, 1192m, 967m, 807s. $^1$H NMR (500 MHz, D$_2$O/NaCl, TSP): 5.82 (d, J=15.2, 6H), 5.81 (d, J=15.6, 4H), 5.71 (d, J=8.5, 2H) 5.65-5.55 (m, 10H), 5.48 (d. J=13.7, 4H), 5.39 (br, 2H) 4.49 (d, J=13.7, 4H), 4.37 (d, J=15.6, 4H), 4.30 (d, J=15.2, 4H), 4.28 (d, J=14.0, 2H) $^{13}$C NMR (125 MHz, D$_2$O): 157.5, 157.0, 156.9, 156.7, 71.9, 71.8, 71.7, 71.4, 71.0, 64.4, 53.3, 53.1, 52.7. 51.5. MS (MALDI-TOF): m/z 1163 ([M+H]$^+$). HR-MS (MALDI-TOF): m/z 1163.3186 (100, [M+H]$^+$, $C_{42}H_{43}N_{28}O_{14}$, calcd 1163.3508). Anal. Calcd for $C_{42}H_{42}N_{28}O_{14}\cdot(H2O)_9$: C 38.06, H 4.56, N 29.59. Found: C 38.22, H 4.82, N 29.69.

X-Ray Crystallography.

A colorless plate of iCB[6] with approximate dimensions 0.022×0.230×0.380 mm$^3$, was used for the X-ray crystallographic analysis. The X-ray intensity data were measured at 213(2) K on a three-circle diffractometer system equipped with a Bruker Smart1000 CCD area detector using a graphite monochromator and a MoKα fine-focus sealed tube (λ=0.71073 Å). Data were corrected for absorption effects with the semi-empirical method using SADABS. The structure was solved and refined using the SHELXS-97 and SHELXL-97 software. The final anisotropic full-matrix least-squares refinement on F$^2$ converged to the R values. The diffraction data from a colorless block-shaped crystal of iCB[7] measuring 0.21×0.19×0.06 mm$^3$ mounted on the loop were collected at 100 K on a ADSC Quantum 210 CCD diffractometer with synchrotron radiation (λ=1.00000☐) at Macromolecular Crystallography Wiggler Beamline 4A, Pohang Accelerator Laboratory (PAL), Pohang, Korea. The crystal was rotated through a total of 180°. The autoindexing procedure performed with DENZO indicated that the crystals belong to a rhombohedral space group, with unit-cell parameters a=32.200(5) ☐, c=32.581(7) ☐, λ=120° The raw data were processed and scaled using the program HKL2000. The space group was determined to be R-3. A total of 15222 measured reflections were merged into 6769 independent reflections. The structure was solved by directed methods and refined by full-matrix least-squares method implemented in SHELXTL program package. All the non-hydrogen atoms were refined anisotropically except inclused THF. Hydrogen atoms were added to their geometrically ideal positions. The crystallographic data are summarized in Table S2.

TABLE S1

X-ray crystal data for iCB[6]•H$_2$O$^+$•Cl$^-$•8.7H$_2$O

| | |
|---|---|
| Empirical formula | C36 H56.40 Cl N24 O21.70 |
| Formula weight | 1208.10 |
| Temperature | 213(2) K |
| Wavelength | 0.71073 Å |
| Crystal system | Monoclinic |
| Space group | P 2$_1$ |
| Unit cell dimensions | a = 12.434(2) Å α = 90° |
| | b = 16.122(3) Å β = 104.923(4)° |
| | c = 12.667(2) Å γ = 90° |
| Volume | 2453.6(8) Å$^3$ |
| Z | 2 |
| Density, ρ$_{calc}$ | 1.635 g/cm$^3$ |
| Absorption coefficient, μ | 0.188 mm$^{-1}$ |
| F(000) | 1262 |
| Crystal size | 0.380 0.230 × 0.022 mm$^3$ |
| Index ranges | −14 ≤ h ≤ 10, −18 ≤ k ≤ 19, −14 ≤ l ≤ 14 |
| Reflections collected | 8493 |

TABLE S1-continued

X-ray crystal data for iCB[6]•H$_2$O$^+$•Cl$^-$•8.7H$_2$O

| | |
|---|---|
| Independent reflections | 7318[R(int) − 0.0193] |
| Observed reflection, I > 2σ(I) | 5794 |
| Data/restraints/parameters | 7318/34/850 |
| Goodness-of-fit on F$^2$ | 0.998 |
| Final R indices [I > 2sigma(I)] | R$_1$ = 0.0431, wR$_2$ = 0.0998 |
| R indices (all data) | R$_1$ = 0.0649, wR$_2$ = 0.1129 |
| Largest diff. peak and hole | 0.400 and −0.311 e$^-$/Å$^3$ |

$R_1 = \Sigma||F_o| - |F_c||/\Sigma|F_o|, wR2 = [\Sigma w(F_o^2 - F_c^2)^2/\Sigma w(F_o^2)^2]^{1/2}$

TABLE S2

X-ray crystal data for iCB[7]•THF•14H$_2$O.

| | |
|---|---|
| Empirical formula | C46 H78 N28 O29 |
| Formula weight | 1487.36 |
| Temperature | 100(2) K |
| Wavelength | 1.00000 Å $^a$ |
| Crystal system | Rhombohedral |
| Space group | R-3 |
| Unit cell dimensions | a~32.200(5) Å α = 90° |
| | b = 32.200(5) Å β = 90° |
| | c = 32.581(7) Å γ = 120° |
| Volume | 29255(8) Å$^3$ |
| Z | 18 |
| Density (calculated) | 1.520 g/cm$^3$ |
| Absorption coefficient | 0.301 mm$^{-1}$ |
| F(000) | 14076 |
| Crystal size | 0.21 × 0.19 × 0.06 mm$^3$ |
| Index ranges | −18 ≤ h ≤ 32, −32 ≤ k ≤ 21, −32 ≤ l ≤ 27 |
| Reflections collected | 15222 |
| Independent reflections | 6769 [R(int) = 0.0992] |
| Observed reflection, I > 2σ(I) | 5794 |
| Data/restraints/parameters | 6769/217/1002 |
| Goodness-of-fit on F$^2$ | 1.613 |
| Final R indices [I > 2sigma(I)] | R$_1$ = 0.0967, wR$_2$ = 0.3179 |
| R indices (all data) | R$_1$ = 0.0979, wR$_2$ = 0.3226 |
| Extinction coefficient | 0.00046(9) |
| Largest diff. peak and hole | 1.173 and −0.797 e$^-$/Å$^3$ |

$R_1 = \Sigma||F_o| - |F_{ci}||/\Sigma|F_o|, wR2 = [\Sigma w(F_o^2 - F_c^2)^2/\Sigma w(F_o^2)^2]^{1/2}$ $^a$ The x-ray data were collected with synchrotron radiation at Macromolecular Crystallography Wiggler Beamline 4A, Pohang Accelerator Laboratory (PAL).

The implications of i-CB[n] compounds and/or derivatives for the CB[n] research are clear and many. First, the i-CB[n] compounds of large ring size can be synthesized with unprecedented size and shape selectively. Second, synthetic and mechanistic studies indicate that the preparation and isolation of i-CB[n] compounds of large ring sizes, i.e. i-CB[12]-i-CB [25], and with larger numbers of inverted glycoluril units is readily effected. Third, functional groups such as —OH or CO$_2$H may be introduced to the inverted unit to directly interact with guests within their hydrophobic cavity.

Generally, the CB[n] compounds and/or derivatives, and i-CB[n] compounds and/or derivatives of the present invention may have an internal volume cavity of up to about 10,000 Å$^3$. However, explicitly contemplated herein are internal volume cavities in the ranges of 300 to 600 Å$^3$, 300 to 1,200 Å$^3$, 300 to 1,800 Å$^3$, 300 to 3,000 Å$^3$, 300 and 6,000 Å$^3$ and 300 and 9,000 Å$^3$.

FIGS. 4 and 6-23 provide various types of instrumental characterizations of exemplary i-CB[n] compounds using known instrumental procedures.

FIG. 5 depicts a view of introverted CB[6] from crystal structure data. Anisotropic atomic displacement ellipsoids for the non-hydrogen atoms are shown at the 50% probability level. Inverted hydrogen atoms are conspicuously protruding into the molecular cavity.

Figure 24:
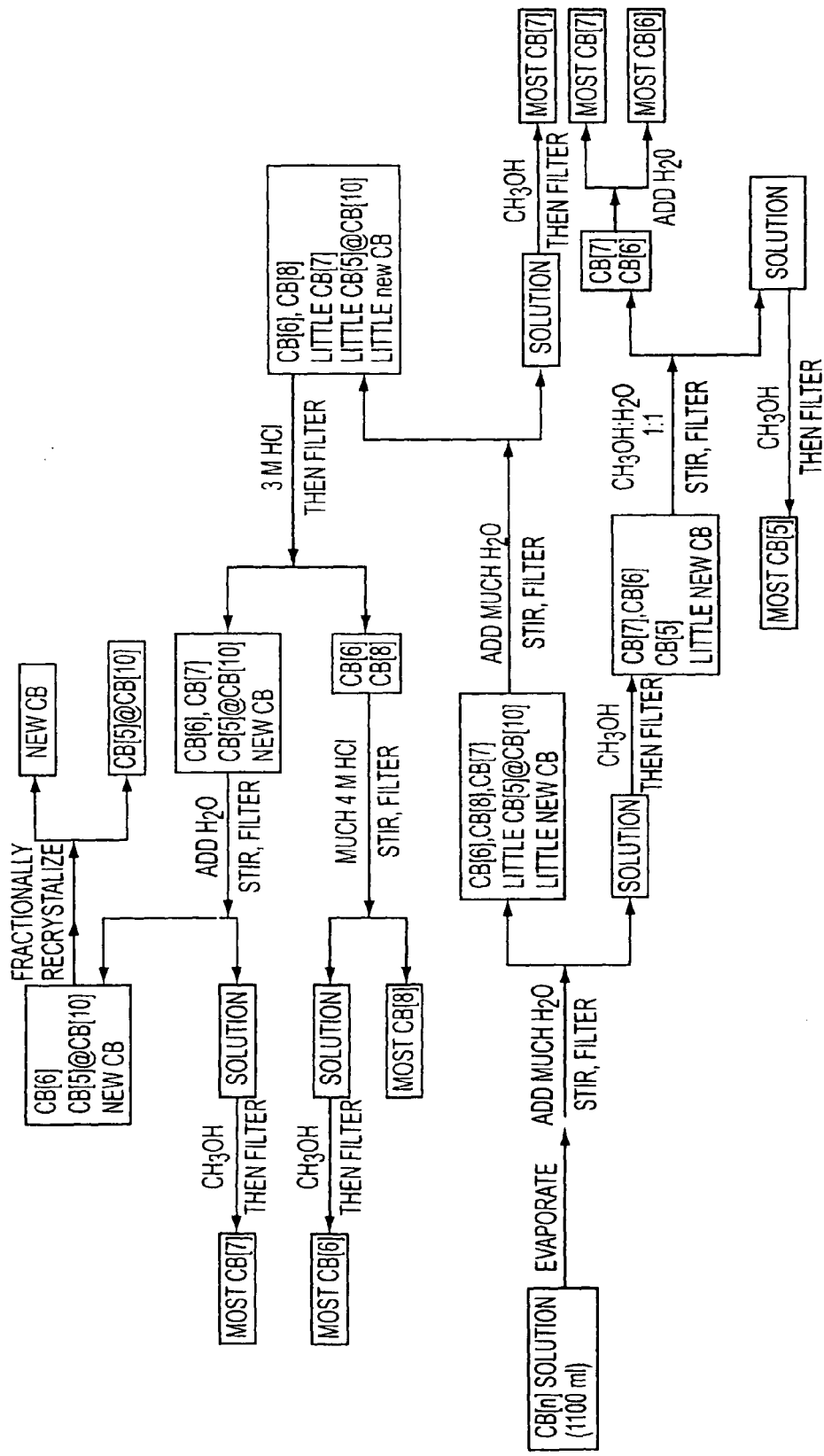
FIG. 24 is a flowchart for the separation of a CB[n] compounds from a mixture.

FIG. 24 illustrates a flow diagram for the separation of various extroverted and introverted CB[n] compounds.

Although the diagram does not show i-CB[7], i-CB[7] may be separated from i-CB[6] as described herein. These procedures may be used with routine modification, if required, to isolate other CB[n] and i-CB[n] compounds, particularly where n>8.

The following abbreviations have been used in the above specification.
- i) DQF COSY: Double Quantum Filtered-Correlation Spectroscopy
- ii) ROESY: Rotating Frame Overhauser Effect Spectroscopy
- iii) NOEs: Nuclear Overhauser Effect
- iv) HSQC: Heteronuclear Single Quantum Correlation
- v) MALDI-TOF: Matrix-Assisted Laser Desorption/Ionization Time of Flight (Mass Spectrometry)
- vi) ES-MS: Electro-Spray Mass Spectrometry The above procedures may be used in a straightforward manner to produce CB[n] compounds and/or derivatives, and/or i-CB[n] compounds and/or derivatives of selective size and substitution patterns. Of particular note is that specific compounds can be produced, isolated and easily characterized.

Further guest compounds which may be hosted by the present CB[n] compounds and/or derivatives, and i-CB[n] compounds and/or derivatives may have a molecular weight of up to about 1,000 daltons, preferably up to about 500 daltons. Examples of specific guest compounds are pharmaceutically active compounds and/or biologically active amines, such as dopamine or acetylcholine.

Additionally, the inverted CB[n] compounds and/or derivatives of the present invention compliment the extroverted CB[n] compounds and/or derivatives of co-pending U.S. Ser. No. 10/933,538, catalysts, and components of molecular machines, for example.

What is claimed is:

1. An isolated, introverted cucurbituril compound having at least one hydrogen atom pointing into an internal molecular cavity of the compound, the introverted cucurbituril compound being selected from the group consisting of i-CB[5], i-CB[6], i-CB[7], i-CB[8], i-CB[9] and i-CB[10].

2. The isolated, introverted cucurbituril compound of claim 1, which monointroverted.

3. The isolated, introverted cucurbituril compound of claim 1, which is multiply-introverted.

4. The isolated, introverted cucurbituril compound of claim 1, which is i-CB[6].

5. The isolated, introverted cucurbituril compound of claim 1, which is i-CB[7].

6. The isolated, introverted cucurbituril compound of claim 1, which is i-CB[8].

7. The isolated, introverted cucurbituril compound of claim 1, which is i-CB[9].

8. The isolated, introverted cucurbituril compound of claim 1, which is i-CB[10].

9. The isolated, introverted cucurbituril compound of claim 1, which is selected from the group consisting of i-CB[5], i-CB[6], i-CB[7] and i-CB[8].

10. The isolated, introverted cucurbituril compound of claim 1, which is purified.

11. The isolated, introverted cucurbituril compound of claim 1, which contains a guest compound in the internal molecular cavity of the compound.

12. The isolated, introverted cucurbituril compound of claim 11, which is purified.

13. A solution, comprising an introverted cucurbituril compound, which compound has at least one hydrogen atom pointing into an internal molecular cavity of the compound, the introverted cucurbituril compound being selected from the group consisting of i-CB[5], i-CB[6], i-CB[7], i-CB[8], i-CB[9] and i-CB[10], and which compound contains a guest compound in the internal molecular cavity thereof; and a solvent.

* * * * *